(12) United States Patent
Hanssen et al.

(10) Patent No.: US 8,535,385 B2
(45) Date of Patent: Sep. 17, 2013

(54) PROSTHETIC IMPLANT SUPPORT STRUCTURE

(75) Inventors: Arlen D. Hanssen, Rochester, MN (US); David G. Lewallen, Rochester, MN (US)

(73) Assignee: Zimmer, Inc., Warsaw, IN (US)

( * ) Notice: Subject to any disclaimer, the term of this patent is extended or adjusted under 35 U.S.C. 154(b) by 108 days.

(21) Appl. No.: 13/205,163

(22) Filed: Aug. 8, 2011

(65) Prior Publication Data
US 2011/0295382 A1 Dec. 1, 2011

Related U.S. Application Data

(60) Continuation of application No. 11/560,276, filed on Nov. 15, 2006, which is a division of application No. 10/225,774, filed on Aug. 22, 2002, now abandoned.

(60) Provisional application No. 60/315,148, filed on Aug. 27, 2001.

(51) Int. Cl.
*A61F 2/36* (2006.01)

(52) U.S. Cl.
USPC ............... 623/23.19; 623/23.28; 623/23.3

(58) Field of Classification Search
USPC .......... 623/20.15, 20.32, 20.34, 23.46, 20.16, 623/20.17, 23.15–23.35
See application file for complete search history.

(56) References Cited

U.S. PATENT DOCUMENTS

| | | | |
|---|---|---|---|
| 2,947,308 A | 8/1960 | Gorman | |
| 3,605,123 A * | 9/1971 | Hahn | 623/23.55 |
| 3,658,056 A | 4/1972 | Huggler et al. | |
| D230,429 S | 2/1974 | Davidson et al. | |
| 3,855,638 A | 12/1974 | Pilliar | |
| 3,871,031 A | 3/1975 | Boutin | |
| 3,891,997 A | 7/1975 | Herbert | |

(Continued)

FOREIGN PATENT DOCUMENTS

| | | |
|---|---|---|
| AU | 2004203348 A1 | 9/2005 |
| CA | 2473633 A1 | 9/2005 |

(Continued)

OTHER PUBLICATIONS

U.S. Appl. No. 10/225,774, Advisory Action mailed Oct. 26, 2005, 3 pgs.

(Continued)

*Primary Examiner* — Paul Prebilic
(74) *Attorney, Agent, or Firm* — Schwegman, Lundberg & Woessner P.A.

(57) ABSTRACT

A prosthetic system that includes a prosthetic implant and a support structure secured to an inner surface of the cavity in the end of the bone is disclosed. The support structure defines a channel that extends through the length of the support structure. The prosthetic implant is received in the channel, and a portion of the prosthetic implant is secured to an inner surface of the channel by an adhesive. The stem of the prosthesis beyond the channel may be cemented or uncemented. The support structure may have an approximately funnel shape. The support structure may be a hollow porous cylindrical sleeve. The support structure may comprise a pair of partially hemispherical components arranged in spaced apart relationship thereby defining a channel between the pair of components. The support structure may comprise a plurality of pedestals secured to the inner surface of the cavity of the bone.

30 Claims, 9 Drawing Sheets

(56) References Cited

U.S. PATENT DOCUMENTS

| | | |
|---|---|---|
| 3,903,549 A | 9/1975 | Deyerle |
| 3,906,550 A * | 9/1975 | Rostoker et al. ............ 623/23.55 |
| 3,918,102 A | 11/1975 | Eichler |
| 4,064,567 A | 12/1977 | Burstein et al. |
| 4,136,405 A | 1/1979 | Pastrick et al. |
| 4,164,794 A | 8/1979 | Spector et al. |
| 4,206,516 A | 6/1980 | Pilliar |
| 4,216,549 A | 8/1980 | Hillberry et al. |
| 4,219,893 A | 9/1980 | Noiles |
| 4,224,696 A | 9/1980 | Murray et al. |
| 4,404,691 A | 9/1983 | Buning et al. |
| 4,444,061 A | 4/1984 | Mathias et al. |
| 4,523,587 A | 6/1985 | Frey |
| 4,549,319 A | 10/1985 | Meyer |
| 4,659,331 A | 4/1987 | Matthews et al. |
| 4,662,891 A | 5/1987 | Noiles |
| 4,678,470 A | 7/1987 | Nashef et al. |
| 4,711,639 A | 12/1987 | Grundei |
| 4,718,909 A | 1/1988 | Brown |
| 4,735,625 A | 4/1988 | Davidson |
| 4,778,473 A | 10/1988 | Matthews et al. |
| 4,789,663 A | 12/1988 | Wallace et al. |
| 4,790,852 A | 12/1988 | Noiles |
| 4,822,366 A | 4/1989 | Bolesky |
| 4,827,919 A | 5/1989 | Barbarito et al. |
| 4,828,565 A | 5/1989 | Duthoit et al. |
| 4,834,759 A | 5/1989 | Spotorno et al. |
| 4,878,919 A | 11/1989 | Pavlansky et al. |
| 4,883,448 A | 11/1989 | Kobayashi et al. |
| 4,883,488 A | 11/1989 | Bloebaum et al. |
| 4,888,021 A | 12/1989 | Forte et al. |
| 4,936,859 A * | 6/1990 | Morscher et al. ........... 623/23.46 |
| 4,944,757 A | 7/1990 | Martinez et al. |
| 4,950,298 A | 8/1990 | Gustilo et al. |
| 4,988,359 A | 1/1991 | Frey et al. |
| 5,019,103 A | 5/1991 | Van Zile et al. |
| 5,032,134 A | 7/1991 | Lindwer |
| 5,059,196 A | 10/1991 | Coates |
| 5,092,897 A | 3/1992 | Forte |
| 5,108,446 A | 4/1992 | Wagner et al. |
| 5,133,771 A | 7/1992 | Duncan et al. |
| 5,152,797 A | 10/1992 | Luckman et al. |
| 5,156,626 A | 10/1992 | Broderick et al. |
| 5,163,966 A | 11/1992 | Norton et al. |
| 5,176,711 A | 1/1993 | Grimes |
| 5,197,488 A | 3/1993 | Kovacevic |
| 5,211,664 A | 5/1993 | Tepic et al. |
| 5,222,984 A | 6/1993 | Forte |
| 5,226,915 A | 7/1993 | Bertin |
| 5,246,459 A | 9/1993 | Elias |
| 5,356,414 A | 10/1994 | Cohen et al. |
| 5,356,629 A | 10/1994 | Sander et al. |
| 5,358,527 A | 10/1994 | Forte |
| 5,358,530 A | 10/1994 | Hodorek |
| 5,370,693 A | 12/1994 | Kelman et al. |
| 5,376,123 A | 12/1994 | Klaue et al. |
| 5,387,241 A | 2/1995 | Hayes |
| 5,405,394 A | 4/1995 | Davidson |
| 5,413,604 A | 5/1995 | Hodge |
| 5,443,512 A * | 8/1995 | Parr et al. ................... 623/23.51 |
| 5,462,563 A | 10/1995 | Shearer et al. |
| 5,480,445 A | 1/1996 | Burkinshaw |
| 5,489,311 A | 2/1996 | Cipolletti |
| 5,507,830 A | 4/1996 | DeMane et al. |
| 5,510,396 A | 4/1996 | Prewett et al. |
| 5,531,791 A | 7/1996 | Wolfinbarger et al. |
| 5,549,685 A | 8/1996 | Hayes |
| 5,571,198 A | 11/1996 | Drucker et al. |
| 5,591,233 A | 1/1997 | Kelman et al. |
| 5,609,645 A | 3/1997 | Vinciguerra |
| 5,658,338 A | 8/1997 | Tullos et al. |
| 5,658,349 A | 8/1997 | Brooks et al. |
| 5,662,158 A | 9/1997 | Caldarise |
| 5,683,467 A | 11/1997 | Pappas |
| 5,702,478 A | 12/1997 | Tornier |
| 5,702,483 A | 12/1997 | Kwong |
| 5,734,959 A | 3/1998 | Krebs et al. |
| 5,766,256 A | 6/1998 | Oudard et al. |
| 5,782,925 A | 7/1998 | Collazo et al. |
| 5,782,929 A | 7/1998 | Sederholm |
| 5,788,976 A | 8/1998 | Bradford |
| 5,824,103 A | 10/1998 | Williams |
| 5,858,020 A | 1/1999 | Johnson et al. |
| 5,871,548 A | 2/1999 | Sanders et al. |
| 5,879,393 A | 3/1999 | Whiteside |
| 5,910,172 A | 6/1999 | Penenberg |
| 5,931,409 A | 8/1999 | Nulle et al. |
| 5,957,979 A | 9/1999 | Beckman et al. |
| 5,958,314 A | 9/1999 | Draenert |
| 5,972,368 A | 10/1999 | McKay |
| 5,976,148 A | 11/1999 | Charpenet et al. |
| 5,984,968 A | 11/1999 | Park |
| 5,993,716 A | 11/1999 | Draenert |
| 5,997,581 A | 12/1999 | Khalili |
| 6,008,432 A | 12/1999 | Taylor |
| 6,013,080 A | 1/2000 | Khalili |
| 6,039,764 A | 3/2000 | Pottenger et al. |
| 6,042,612 A | 3/2000 | Voydeville |
| 6,053,945 A | 4/2000 | O'Neil et al. |
| 6,074,423 A | 6/2000 | Lawson |
| 6,074,424 A | 6/2000 | Perrone et al. |
| 6,080,195 A | 6/2000 | Colleran et al. |
| 6,117,175 A | 9/2000 | Bosredon |
| 6,126,691 A | 10/2000 | Kasra et al. |
| 6,136,029 A | 10/2000 | Johnson et al. |
| 6,139,581 A | 10/2000 | Engh et al. |
| 6,139,584 A | 10/2000 | Ochoa et al. |
| 6,142,998 A | 11/2000 | Smith et al. |
| 6,162,254 A | 12/2000 | Timoteo |
| 6,162,255 A | 12/2000 | Oyola |
| 6,171,342 B1 | 1/2001 | O'Neil |
| 6,264,699 B1 | 7/2001 | Noies |
| 6,290,725 B1 | 9/2001 | Weiss et al. |
| 6,328,764 B1 | 12/2001 | Mady |
| 6,355,069 B1 | 3/2002 | DeCarlo, Jr. et al. |
| 6,368,352 B1 | 4/2002 | Camino et al. |
| 6,423,096 B1 | 7/2002 | Musset et al. |
| 6,428,578 B2 | 8/2002 | White |
| 6,447,549 B1 | 9/2002 | Taft |
| 6,458,161 B1 | 10/2002 | Gibbs et al. |
| 6,613,092 B1 | 9/2003 | Kana et al. |
| 6,699,293 B2 | 3/2004 | White |
| 6,797,006 B2 | 9/2004 | Hodorek |
| 6,843,806 B2 | 1/2005 | Haves et al. |
| 6,875,218 B2 | 4/2005 | Dye et al. |
| 6,875,237 B2 | 4/2005 | Dye et al. |
| 6,926,740 B2 | 8/2005 | Lewis et al. |
| 6,946,001 B2 | 9/2005 | Sanford et al. |
| 6,981,991 B2 | 1/2006 | Ferree |
| 7,105,026 B2 | 9/2006 | Johnson et al. |
| 7,179,295 B2 | 2/2007 | Kovacevic |
| 7,179,296 B2 | 2/2007 | Dooney |
| 7,179,297 B2 | 2/2007 | McLean |
| 7,179,298 B2 | 2/2007 | Greenlee |
| D538,431 S | 3/2007 | Botha |
| 7,238,208 B2 | 7/2007 | Camino et al. |
| 7,264,636 B2 | 9/2007 | Lewis et al. |
| 7,291,174 B2 | 11/2007 | German et al. |
| 7,291,177 B2 | 11/2007 | Gibbs |
| 7,435,263 B2 | 10/2008 | Barnett et al. |
| 7,713,306 B2 | 5/2010 | Gibbs |
| D618,800 S | 6/2010 | Mayon et al. |
| 7,846,212 B2 | 12/2010 | Lewis et al. |
| 7,892,288 B2 | 2/2011 | Blaylock et al. |
| 7,892,289 B2 | 2/2011 | Serafin, Jr. et al. |
| 8,123,814 B2 | 2/2012 | Meridew et al. |
| 8,382,849 B2 | 2/2013 | Thomas |
| D684,693 S | 6/2013 | Hanssen et al. |
| 2002/0151984 A1 | 10/2002 | White |
| 2003/0065397 A1 | 4/2003 | Hanssen et al. |
| 2003/0153981 A1 | 8/2003 | Wang et al. |
| 2003/0163203 A1 | 8/2003 | Nycz et al. |
| 2003/0183025 A1 | 10/2003 | Krstic |
| 2003/0229398 A1 | 12/2003 | Iesaka et al. |

| | | | |
|---|---|---|---|
| 2004/0034432 A1 | 2/2004 | Hughes et al. | |
| 2004/0049270 A1 | 3/2004 | Gewirtz | |
| 2004/0049284 A1 | 3/2004 | German et al. | |
| 2004/0117024 A1 | 6/2004 | Gerbec et al. | |
| 2004/0162619 A1 | 8/2004 | Blaylock et al. | |
| 2004/0172137 A1 | 9/2004 | Blaylock et al. | |
| 2005/0107883 A1 | 5/2005 | Goodfried et al. | |
| 2005/0278034 A1 | 12/2005 | Johnson et al. | |
| 2005/0283254 A1 | 12/2005 | Hayes, Jr. et al. | |
| 2007/0088443 A1 | 4/2007 | Hanssen et al. | |
| 2007/0129809 A1 | 6/2007 | Meridew et al. | |
| 2008/0167722 A1 | 7/2008 | Metzger et al. | |
| 2008/0281430 A1 | 11/2008 | Kelman et al. | |
| 2010/0145452 A1 | 6/2010 | Blaylock et al. | |
| 2011/0066252 A1 | 3/2011 | Hanssen et al. | |
| 2011/0112651 A1 | 5/2011 | Blaylock et al. | |
| 2011/0295382 A1 | 12/2011 | Hanssen | |
| 2013/0013078 A1 | 1/2013 | Hanssen et al. | |
| 2013/0013080 A1 | 1/2013 | Hanssen et al. | |
| 2013/0018478 A1 | 1/2013 | Hanssen et al. | |

FOREIGN PATENT DOCUMENTS

| | | | |
|---|---|---|---|
| EP | 0336774 B1 | 12/1992 | |
| EP | 0532585 B1 | 4/2000 | |
| EP | 1004283 A2 | 5/2000 | |
| EP | 0863731 B1 | 4/2001 | |
| EP | 1004283 A3 | 3/2002 | |
| EP | 1004283 B1 | 5/2005 | |
| FR | 2772593 A1 | 6/1999 | |
| GB | 2223172 A | 4/1990 | |
| JP | 6-169930 A | 6/1994 | |
| JP | 10-277069 A | 10/1998 | |
| JP | 2000-185062 A | 7/2000 | |
| JP | 2001-503283 T | 3/2001 | |
| JP | 2001-526573 T | 12/2001 | |
| JP | 2004-016822 A | 1/2004 | |
| JP | 2005-246036 A | 9/2005 | |
| WO | WO97/30661 A1 | 8/1997 | |
| WO | WO-9932053 A1 | 7/1999 | |
| WO | WO02/5732 A1 | 1/2002 | |
| WO | WO-2009089581 A1 | 7/2009 | |

OTHER PUBLICATIONS

U.S. Appl. No. 10/225,774, Examiner Interview Summary Mar. 17, 2005, 4 pgs.
U.S. Appl. No. 10/225,774, Final Office Action mailed Jun. 6, 2005, 9 pgs.
U.S. Appl. No. 10/225,774, Final Office Action mailed Aug. 17, 2006, 8 pgs.
U.S. Appl. No. 10/225,774, Non-Final Office Action mailed Feb. 8, 2006, 6 pgs.
U.S. Appl. No. 10/225,774, Non-Final Office Action mailed Jun. 30, 2004, 5 pgs.
U.S. Appl. No. 10/225,774, Non-Final Office Action mailed Dec. 8, 2004, 6 pgs.
U.S. Appl. No. 10/225,774, Response filed Mar. 7, 2005 to Non-Final Office Action mailed Dec. 8, 2004, 21 pgs.
U.S. Appl. No. 10/225,774, Response filed Apr. 16, 2004 to Restriction Requirement mailed Mar. 17, 2004, 1 pg.
U.S. Appl. No. 10/225,774, Response filed Jun. 7, 2006 to Non-Final Office Action mailed Feb. 8, 2006, 21 pgs.
U.S. Appl. No. 10/225,774, Response filed Sep. 20, 2004 to Non-Final Office Action mailed Jun. 30, 2004, 14 pgs.
U.S. Appl. No. 10/225,774, Response filed Oct. 6, 2005 to Final Office Action mailed Jun. 6, 2005, 21 pgs.
U.S. Appl. No. 10/225,774, Response filed Nov. 15, 2006 to Final Office Action mailed Aug. 17, 2006, 1 pg.
U.S. Appl. No. 10/225,774, Restriction Requirement mailed Mar. 17, 2004, 6 pgs.
U.S. Appl. No. 10/780,378, Preliminary Amendment filed Jun. 1, 2004, 20 pgs.
U.S. Appl. No. 10/780,378, Restriction Requirement Dec. 4, 2006, 6 pgs.
U.S. Appl. No. 10/794,721, Final Office Action mailed May 6, 2010, 8 pgs.
U.S. Appl. No. 10/794,721, Non-Final Office Action mailed Jun. 15, 2009, 9 pgs.
U.S. Appl. No. 10/794,721, Notice of Allowance mailed Oct. 14, 2010, 6 pgs.
U.S. Appl. No. 10/794,721, Response filed Feb. 2, 2007 to Non Final Office Action mailed Nov. 2, 2006, 7 pgs.
U.S. Appl. No. 10/794,721, Response filed Apr. 14, 2009 to Final Office Action mailed Jan. 16, 2009, 8 pgs.
U.S. Appl. No. 10/794,721, Response filed Jun. 16, 2008 to Final Office Action mailed Jan. 16, 2008, 8 pgs.
U.S. Appl. No. 10/794,721, Response filed Sep. 28, 2009 to Non Final Office Action mailed Jun. 15, 2009, 10 pgs.
U.S. Appl. No. 10/794,721, Response filed Oct. 6, 2010 to Final Office Action mailed May 6, 2010, 6 pgs.
U.S. Appl. No. 10/794,721, Response filed Oct. 8, 2008 to Non Final Office Action mailed Jul. 8, 2008, 8 pgs.
U.S. Appl. No. 10/794,721, Response filed Nov. 8, 2007 to Non Final Office Action mailed Aug. 3, 2007, 7 pgs.
U.S. Appl. No. 10/794,721, Supplemental Response filed Feb. 8, 2010 to Non Final Office Action mailed Jan. 12, 2010, 2 pgs.
U.S. Appl. No. 10/794,721, Supplemental Response filed May 18, 2007 to Non Final Office Action mailed Nov. 2, 2006, 7 pgs.
U.S. Appl. No. 11/560,276, Examiner Interview Summary mailed Jan. 18, 2012, 4 pgs.
U.S. Appl. No. 11/560,276, Examiner Interview Summary mailed Jun. 5, 2012, 3 pgs.
U.S. Appl. No. 11/560,276, Final Office Action mailed Mar. 27, 2012, 8 pgs.
U.S. Appl. No. 11/560,276, Response filed Jun. 27, 2012 to Final Office Action mailed Mar. 27, 2012, 12 pgs.
U.S. Appl. No. 12/886,297, Final Office Action mailed Nov. 16, 2012, 6 pgs.
U.S. Appl. No. 12/886,297, Non Final Office Action mailed Jun. 21, 2012, 10 pgs.
U.S. Appl. No. 12/886,297, Response filed May 7, 2012 to Restriction Requirement mailed Mar. 6, 2012, 2 pgs.
U.S. Appl. No. 12/886,297, Response filed Oct. 22, 2012 to Non Final Office Action mailed Jun. 21, 2012, 19 pgs.
U.S. Appl. No. 12/886,297, Restriction Requirement mailed Mar. 6, 2012, 6 pgs.
U.S. Appl. No. 12/946,132, Examiner Interview Summary mailed Jun. 5, 2012, 3 pgs.
U.S. Appl. No. 12/946,132, Final Office Action mailed Jul. 25, 2012, 12 pgs.
U.S. Appl. No. 12/946,132, Non Final Office Action mailed Mar. 28, 2012, 10 pgs.
U.S. Appl. No. 12/946,132, Response filed Jun. 27, 2012 to Non Final Office Action mailed Mar. 28, 2012, 15 pgs.
U.S. Appl. No. 12/946,132, Response filed Sep. 6, 2011 to Restriction Requirement mailed Aug. 23, 2011, 8 pgs.
U.S. Appl. No. 12/946,132, Response filed Sep. 24, 2012 to Final Office Action mailed Jul. 25, 2012, 16 pgs.
U.S. Appl. No. 12/946,132, Restriction Requirement mailed Aug. 23, 2011, 8 pgs.
U.S. Appl. No. 13/007,225, Non Final Office Action mailed Nov. 19, 2012, 9 pgs.
U.S. Appl. No. 13/007,225, Preliminary Amendment filed Jan. 14, 2011, 4 pgs.
U.S. Appl. No. 13/007,225, Response filed Oct. 22, 2012 to Restriction Requirement mailed Sep. 20, 2012, 10 pgs.
U.S. Appl. No. 13/007,225, Restriction Requirement mailed Sep. 20, 2012, 8 pgs.
U.S. Appl. No. 13/007,225, Supplemental Preliminary Amendment filed Sep. 23, 2011, 8 pgs.
U.S. Appl. No. 13/619,190, Preliminary Amendment filed Oct. 29, 2012, 8 pgs.
U.S. Appl. No. 29/379,094, filed Nov. 15, 2010, 6 pgs.
U.S. Appl. No. 29/379,094, Response filed Nov. 21, 2012 to Restriction Requirement mailed Oct. 23, 2012, 4 pgs.
U.S. Appl. No. 29/379,094, Restriction Requirement mailed Oct. 23, 2012, 7 pgs.
Australian Application No. 2004203348, Office Action mailed Jan. 13, 2010, 3 pgs.

Canadian Application No. 2,473,633, Office Action mailed Mar. 12, 2010, 3 pgs.
European Application No. 04254352.0, European Search Report mailed Jun. 22, 2005, 3 pgs.
Femoral/Tibial Augmentation Orthopaedic Salvage System, Biomet Orthopedics, Inc., Product Brochure, (2003, 2004), 12 pgs.
Restriction Requirement mailed Aug. 21, 2009 in related U.S. Appl. No. 11/560,276.
Election filed Oct. 21, 2009 in related U.S. Appl. No. 11/560,276.
Office action mailed Mar. 3, 2010 in related U.S. Appl. No. 11/560,276.
Amendment filed Aug. 2, 2010 in related U.S. Appl. No. 11/560,276.
Office action mailed Oct. 8, 2010 in related U.S. Appl. No. 11/560,276.
Amendment filed Feb. 7, 2011 in related U.S. Appl. No. 11/560,276.
Office action mailed Aug. 11, 2011 n related U.S. Appl. No. 11/560,276.
Amendment filed Feb. 13, 2012 in related U.S. Appl. No. 11/560,276.
Restriction Requirement mailed Aug. 25, 2006 in parent U.S. Appl. No. 10/780,378.
Election filed Sep. 15, 2006 in parent U.S. Appl. No. 10/780,378.
Election filed Jan. 4, 2007 in parent U.S. Appl. No. 10/780,378.
Amendment filed Jun. 15, 2007 in parent U.S. Appl. No. 10/780,378.
Amendment filed Oct. 31, 2007 in parent U.S. Appl. No. 10/780,378.
Amendment filed May 28, 2008 in parent U.S. Appl. No. 10/780,378.
Amendment filed Nov. 12, 2008 in parent U.S. Appl. No. 10/780,378.
Amendment filed Jun. 24, 2009 in parent U.S. Appl. No. 10/780,378.
Restriction Requirement mailed Oct. 22, 2009 in parent U.S. Appl. No. 10/780,378.
Election filed Dec. 22, 2009 in parent U.S. Appl. No. 10/780,378.
Final Office Action mailed Apr. 20, 2010 in parent U.S. Appl. No. 10/780,378.
The Japanese office action mailed May 26, 2009, in related Japanese Patent Application No. 2004-216179.
Office Action mailed Nov. 2, 2006 in related U.S. Appl. No. 10/794,721.
Office Action mailed Aug. 3, 2007 in related U.S. Appl. No. 10/794,721.
Final Office Action mailed Jan. 16, 2008 in related U.S. Appl. No. 10/794,721.
Office Action mailed Jul. 8, 2008 in related U.S. Appl. No. 10/794,721.
Final Office Action mailed Jan. 16, 2009 in related U.S. Appl. No. 10/794,721.
Office Action mailed Jun. 15, 2009 in related U.S. Appl. No. 10/794,721.
Restriction Requirement mailed Dec. 4, 2006 in U.S. Appl. No. 10/780,378.
Office Action mailed Mar. 30, 2007 in U.S. Appl. No. 10/780,378.
Final Office Action mailed Aug. 27, 2007 in U.S. Appl. No. 10/780,378.
Office Action mailed Dec. 12, 2007 in U.S. Appl. No. 10/780,378.
Final Office Action mailed Aug. 21, 2008 in U.S. Appl. No. 10/780,378.
Office Action mailed Feb. 2, 2009 in U.S. Appl. No. 10/780,378.
U.S. Appl. No. 12/886,297, Preliminary Amendment filed Sep. 20, 2010, 10 pgs.
U.S. Appl. No. 12/886,297, Examiners Interview Summary mailed May 6, 2013, 3 pgs.
U.S. Appl. No. 12/886,297, Non Final Office Action mailed Apr. 22, 2013, 6 pgs.
U.S. Appl. No. 12/886,297, Notice of Allowance mailed Feb. 22, 2013, 10 pgs.
U.S. Appl. No. 12/886,297, Notice of Allowance mailed Jun. 26, 2013, 10 pgs.
U.S. Appl. No. 13/007,225, Examiner Interview Summary mailed May 30, 2013, 23 pgs.
U.S. Appl. No. 13/007,225, Final Office Action mailed Apr. 18, 2013, 10 pgs.
U.S. Appl. No. 13/007,225, Response filed Mar. 12, 2013 to Non-Final Office Action mailed Nov. 19, 2012, 13 pgs.
U.S. Appl. No. 13/416,857, Response filed May 24, 2013 to Non Final Office Action mailed Feb. 25, 2013, 15 pgs.
U.S. Appl. No. 29/379,094, Notice of Allowance mailed Feb. 28, 2013, 12 pgs.
International Application Serial No. PCT/US2013/029251, International Search Report mailed Jun. 19, 2013, 5 pgs.
International Application Serial No. PCT/US2013/029251, Written Opinion mailed Jun. 19, 2013, 7 pgs.

* cited by examiner

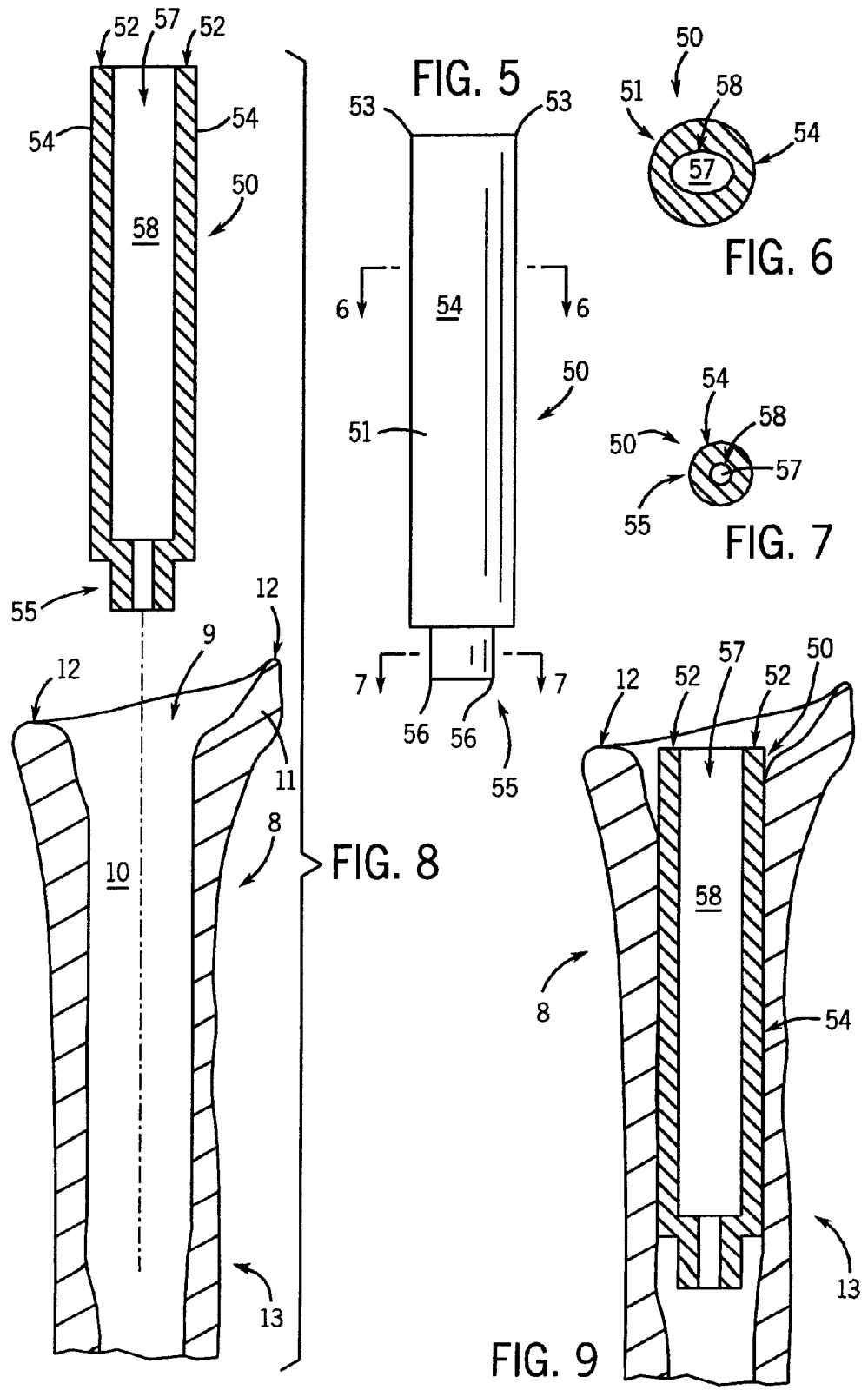

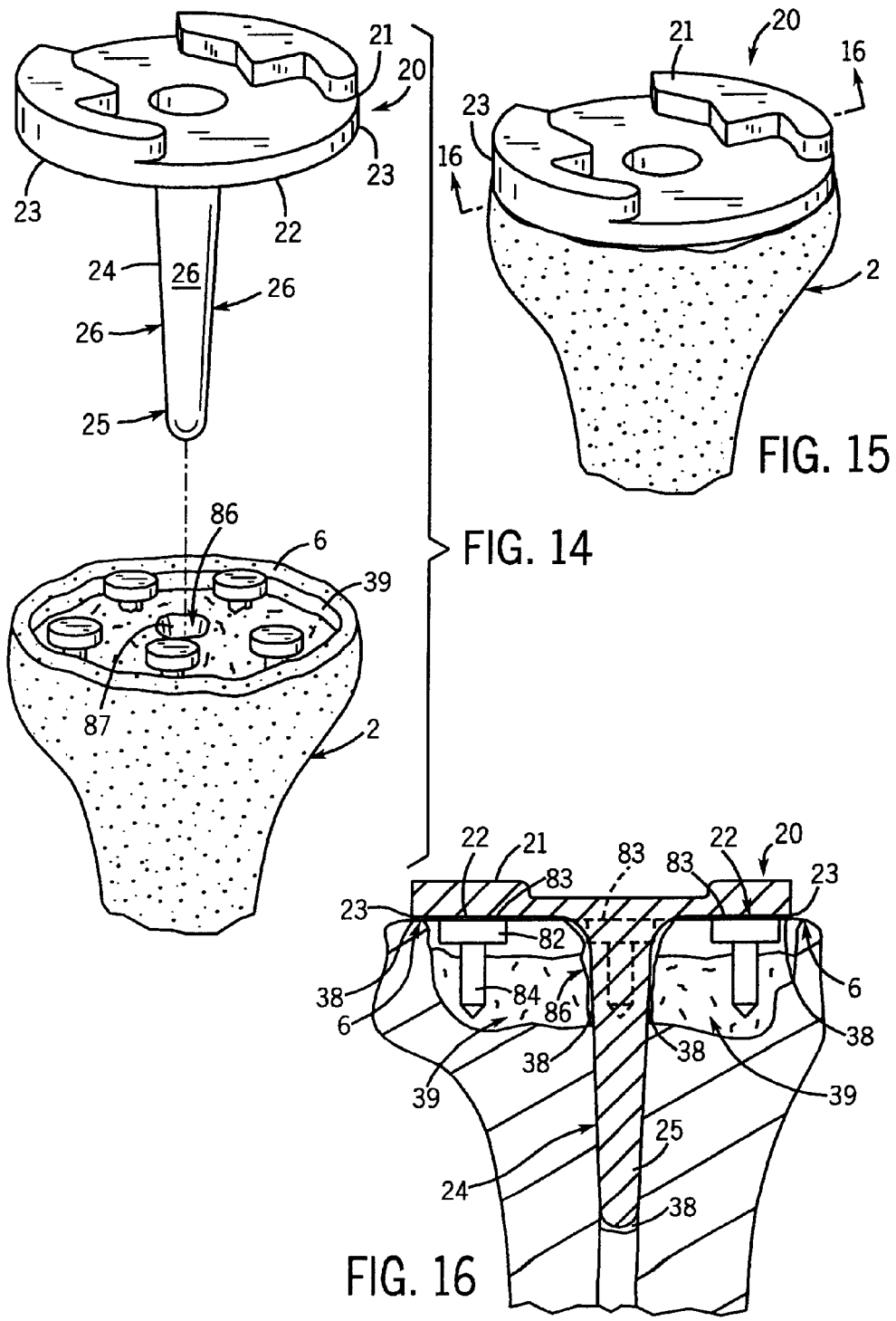

PROSTHETIC IMPLANT SUPPORT STRUCTURE

CROSS-REFERENCE TO RELATED APPLICATIONS

This application is a continuation of U.S. patent application Ser. No. 11/560,276, filed on Nov. 15, 2006 and entitled PROSTHETIC IMPLANT SUPPORT STRUCTURE, which is a division of U.S. patent application Ser. No. 10/225,774, filed on Aug. 22, 2002 and entitled PROSTHETIC IMPLANT SUPPORT STRUCTURE (now abandoned), which claims priority from U.S. Provisional Patent Application Ser. No. 60/315,148, filed on Aug. 27, 2001 and entitled PROSTHETIC IMPLANT SUPPORT STRUCTURE, the entire disclosures of which are hereby expressly incorporated by reference herein.

STATEMENT REGARDING FEDERALLY SPONSORED RESEARCH

Not Applicable.

BACKGROUND OF THE INVENTION

1. Field of the Invention

This invention relates to prosthetic devices for implantation within a bone, and more particularly to support structures that are affixed to a bone and that support prosthetic implants.

2. Description of the Related Art

The replacement of joints, such as the shoulder, hip, knee, ankle and wrist, with prosthetic implants has become widespread. One problem commonly encountered by surgeons replacing joints is the loss of strong bone stock near the joint being replaced. Defects in a bone adjacent a joint, such as the hip or knee, can occur due to wear and arthritis of the joint, congenital deformity, and following the removal of a failed prosthetic implant. Defects can be of a cavitary contained type or segmental and uncontained. Because such bone defects are quite common, various methods have been proposed for minimizing the adverse effects of such bone defects on joint replacement procedures.

It is known to use bone graft to prepare a support surface for a prosthesis, either with or without the use of cement. A bone grafting procedure is often used where there is an appreciable loss of strong bone stock, as is often the case in revision surgery where a previously implanted prosthesis is replaced with a new prosthesis. The support surface prepared with bone graft may be made up entirely of bone graft to substantially surround a prosthesis, or the support surface may be made up of bone graft and the natural bone at the implantation site (for instance, where bone graft is used to fill a relatively small void in the natural bone where the bone is otherwise intact). Bone graft typically includes crushed bone (cancellous and cortical), or a combination of these and synthetic biocompatible materials. Bone graft of this type is intended to stimulate growth of healthy bone. Examples of bone graft materials and related materials can be found in U.S. Pat. Nos. 5,972,368, 5,788,976, 5,531,791, 5,510,396, 5,356,629, 4,789,663 and 4,678,470. Bone graft may be positioned in a bone cavity by various methods such as those described in U.S. Pat. Nos. 6,142,998, 6,013,080 and 5,910,172. The use of bone graft to prepare a support surface for a prosthesis does have certain disadvantages as bone graft may not be readily available in all areas and the devices used to deliver bone graft can be quite cumbersome.

In the presence of bone deficiency, stemmed components are also often used as a method to augment prosthesis fixation during complex primary or revision knee and hip arthroplasty. These stems may be cemented or uncemented; however, the most common method of fixation during revision knee arthroplasty is the use of an uncemented stem combined with cement fixation of the prosthesis in the metaphyseal region. However, due to the large variation of bone quality, interdigitation of bone cement into the metaphyseal region is often suboptimal such that cement fixation of the stem in the bone cavity is necessary. While cement fixation of the stem provides for improved prosthesis fixation, it does have disadvantages. For example, one recognized problem with the use of a cemented stem is that the transfer of stress from the implant to the bone is abnormal. Instead of a normal loading of the bone primarily at the end of the bone near the joint surface, the bone is loaded more distally where the stem of the implant is affixed to the bone. This results in the well known phenomenon called "stress shielding" in which the load (i.e., stress) bypasses or "unloads" the end of the joint surface portion of the bone.

In the presence of severe bone deficiency, the diaphyseal region of the bone is often deficient or absent and requires the use of bone graft or unique prosthetic designs to achieve adequate prosthesis fixation during complex primary or revision knee and hip arthroplasty. The use of large structural allografts to restore bone stock requires a sophisticated bone banking system and is associated with the potential transmission of viral or bacterial pathogens. Furthermore, the difficulties with sizing and bone graft preparation are cumbersome and inexact.

When the bone deficiency occurs at the end surface of a bone, prosthetic implant augmentation devices are also often used. Typically, these devices comprise an implant body and a spacer that is attached to the implant body to form a bearing surface on the implant. The implant is affixed to the bone with the bearing surface resting on the end of the bone, essentially acting as a replacement for lost bone. U.S. Pat. Nos. 5,480,445, 5,387,241, 5,152,797 and 5,019,103 show examples of such devices. While these types of implant augmentation devices provide one solution to the problems associated with the implantation of a prosthesis in the end surface of a bone with inadequate bone stock, these implant augmentation devices can only be used with specific implants available from selected implant manufacturers.

In the context of hip arthroplasty, oversized acetabular components and morselized bone grafts have been used to restore bone deficiencies, but larger defects have in the past been associated with a high failure rate despite efforts at reconstruction using large solid structural allografts or custom acetabular components. These devices gain support against the residual bone of the pelvis but often lack adequate bony support for long term mechanical durability.

Therefore, there is a need for alternative prosthetic implant support structures that do not rely on the use of large amounts of bone graft or cumbersome bone graft delivery devices. There is also a need for prosthetic implant support structures that can eliminate the need to cement the distal portion of the stem of an implant to the inner surface of a bone cavity. In addition, there is a need for prosthetic implant support structures that can be used with a wide variety of prosthetic implants obtained from any number of different implant manufacturers. Furthermore, there is a need for a prosthetic implant system that optimizes implant support on intact host bone with minimal removal of residual host bone and that encourages bone ingrowth and attachment over as large a surface area as possible.

SUMMARY OF THE INVENTION

The foregoing needs are met by a prosthetic system according to the invention that is implanted in a cavity in an end of a bone. The prosthetic system includes a prosthetic implant and a support structure secured to an inner surface of the cavity in the end of the bone. The support structure defines an axial channel that extends through the length of the support structure. The prosthetic implant is received in the channel of the support structure, and a portion of the prosthetic implant is secured to an inner surface of the channel of the support structure by an adhesive.

In one version of the invention, the support structure comprises a hollow sleeve having a sloped outer surface such that the length of a first perimeter of one end of the sleeve is greater than the length of a second perimeter at an opposite end of the sleeve. Such a support structure may have an approximately funnel shape. At the junction of the metaphysis and diaphysis of a bone such as the femur or tibia, the bone defect is often funnel shaped. Accordingly, a funnel shaped support structure in accordance with the invention can be impacted into the distal femur or proximal tibia so that the external geometry of the funnel shaped support structure is firmly wedged in the metaphyseal-diaphyseal junction of the bone. The internal portion of the funnel shaped support structure provides an access channel that allows passage of the stem extending from a traditional prosthesis of any prosthetic design or manufacturer. The stem of the prosthesis is cemented to the inner surface of the access channel using bone cement, and the stem extension beyond the funnel shaped support structure may be cemented or uncemented.

In another version of the invention, the support structure comprises a hollow porous cylindrical sleeve. The sleeve can be inserted into a large cavernous diaphyseal bone defect or can be used as a replacement for segmental or complete diaphyseal bone deficiency. The sleeve can be a number of different sizes and lengths so that a surgeon can pick the appropriate sized sleeve for the patient after intraoperative assessment and thereby avoid difficulties of size mismatch and bone graft contouring. The sleeve can accommodate any number of prosthetic designs and can achieve fixation to remaining host tissue by soft tissue or bone ingrowth. A stem of a prosthesis is fixed within the sleeve by use of bone cement, and the stem of the prosthesis beyond the sleeve may be cemented or uncemented.

In yet another version of the invention, the support structure comprises a pair of components arranged in spaced apart relationship thereby defining a channel between the pair of components. The support structure may be based on hemispherical shapes (such as a configuration approximating a quarter of a sphere) which are provided in a range of sizes for the creation of a prosthetic foundation for support of standard tibial, femoral, or acetabular components. While this support structure is particularly useful in the acetabulum and hip, the support structure is appropriate for all joints undergoing prosthetic replacement with a wide range of shapes and sizes necessary for management of defects in different locations. The support structure is compatible with a range of standard implant designs currently available from a variety of manufacturers. The interface between the pair of components and the prosthetic implant is cemented with bone cement. All surfaces against host bone may be uncemented and are available for bone ingrowth into porous materials used for the components. Optionally, morselized cancellous bone may be placed into fenestrations in the pair of components and supplemental screw fixation of the pair of components to bone may be used to encourage bone ingrowth and secure fixation to host bone over the long term.

In still another version of the invention, the support structure comprises a plurality of pedestals secured to the inner surface of the cavity of the bone. Each pedestal comprises a flat body section and a stem section extending substantially perpendicularly from the body section. The stem section of each pedestal is secured to the inner surface of the cavity of the bone, and the flat body sections of the pedestals are secured to a portion of a bearing surface of the prosthetic implant. The support structure may further comprise bone graft material surrounding the plurality of pedestals. In one form, the pedestals and the bone graft material are arranged in a circular arrangement whereby the channel that extends through the length of the support structure is circular. A stem of a prosthesis is fixed within the channel by use of bone cement, and the stem of the prosthesis beyond the channel may be cemented or uncemented.

It is therefore an advantage of the present invention to provide prosthetic implant support structures that do not rely on the use of large amounts of bone graft or cumbersome bone graft delivery devices.

It is another advantage of the present invention to provide prosthetic implant support structures that can eliminate the need to cement the distal portion of the stem of an implant to the inner surface of a bone cavity.

It is a further advantage of the present invention to provide prosthetic implant support structures that can be used with a wide variety of prosthetic implants obtained from any number of different implant manufacturers.

It is yet another advantage of the present invention to provide a prosthetic implant system that optimizes implant support on intact host bone with minimal removal of residual host bone and that encourages bone ingrowth and attachment over as large a surface area as possible.

These and other features, aspects, and advantages of the present invention will become better understood upon consideration of the following detailed description, drawings, and appended claims.

BRIEF DESCRIPTION OF THE DRAWINGS

FIG. 5 is a side view of another embodiment of a prosthetic implant support structure according to the invention;

FIG. 6 is a cross-sectional view of the prosthetic implant support structure of FIG. 5 taken along line 6-6 of FIG. 5;

FIG. 7 is another cross-sectional view of the prosthetic implant support structure of FIG. 5 taken along line 7-7 of FIG. 5;

FIG. 8 is cross-sectional view of the prosthetic implant support structure of FIG. 5 being placed in a femur;

FIG. 9 is a cross-sectional view of the prosthetic support structure of FIG. 5 as placed in the femur as shown in FIG. 8;

FIG. 14 is an exploded perspective view of a prosthetic implant being placed in the prosthetic support structure of FIG. 12 as placed in the tibia as shown in FIG. 13;

FIG. 15 is a perspective view of a prosthetic implant placed in the prosthetic support structure of FIG. 12 as placed in the tibia as shown in FIG. 13;

FIG. 16 is cross-sectional view of a prosthetic implant placed in the prosthetic support structure as placed in the tibia taken along line 16-16 of FIG. 15;

Figure 1:
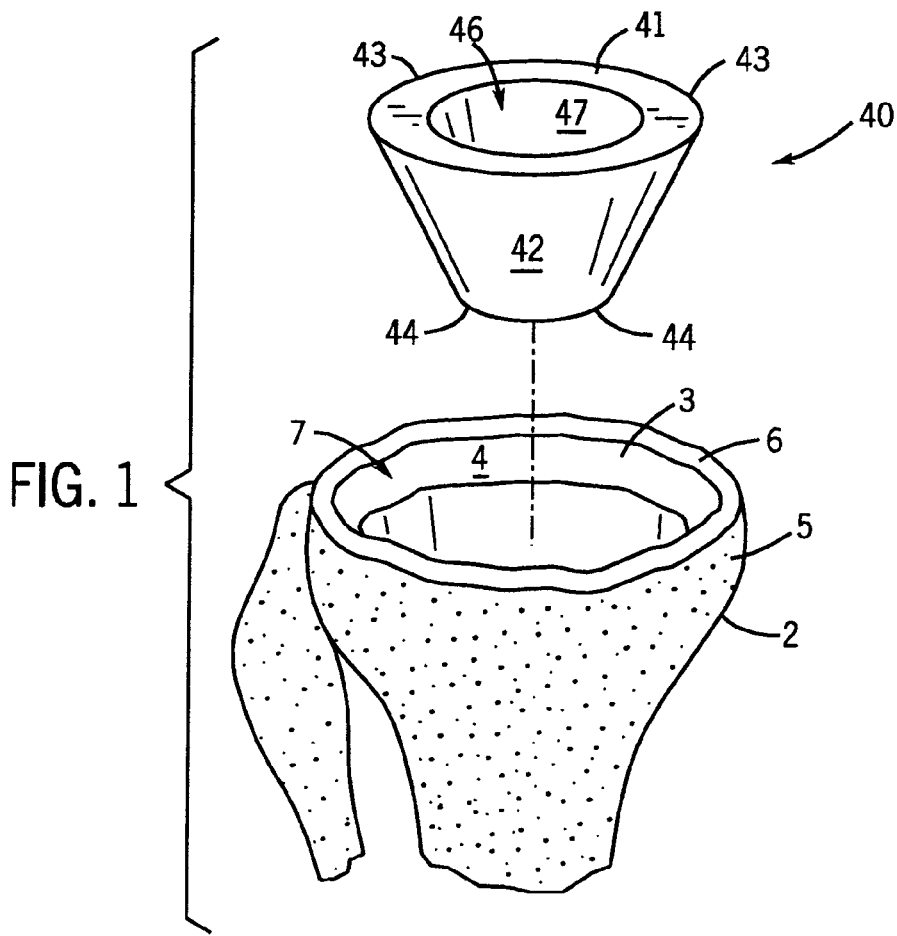
FIG. 1 is an exploded perspective view of one embodiment of a prosthetic implant support structure according to the invention being placed in a tibia.

It should be understood that the drawings are not necessarily to scale and that the embodiments are sometimes illustrated by diagrammatic representations and fragmentary views. In certain instances, details which are not necessary for an understanding of the present invention or which render other details difficult to perceive may have been omitted. It should be understood, of course, that the invention is not necessarily limited to the specific embodiments illustrated herein.

Like reference numerals will be used to refer to like or similar parts from Figure to Figure in the following description of the drawings.

DETAILED DESCRIPTION OF THE INVENTION

The present invention is directed to a prosthetic system that includes a prosthetic implant and a support structure secured to an inner surface of the cavity in the end of the bone. The prosthetic system and the methods for its use are illustrated and described herein with reference to the replacement of a hip joint or a knee joint. However, it should be understood that the methods and prosthetic systems according to the invention can be used in the repair of any bone or in connection with the implantation of prosthetic devices at or in any bone in the body, adjacent to or remote from any joint, including without limitation the hip, knee and spinal joints. Further, the methods and prosthetic systems according to the invention can be used in primary surgery, in which a prosthesis is being used to reconstruct a joint for the first time, as well as in revision surgery, in which a previously-implanted prosthesis is being replaced with another prosthesis. Press fit, cement or other fixation techniques can be employed in conjunction with the methods and prosthetic systems according to the invention.

Figure 2:
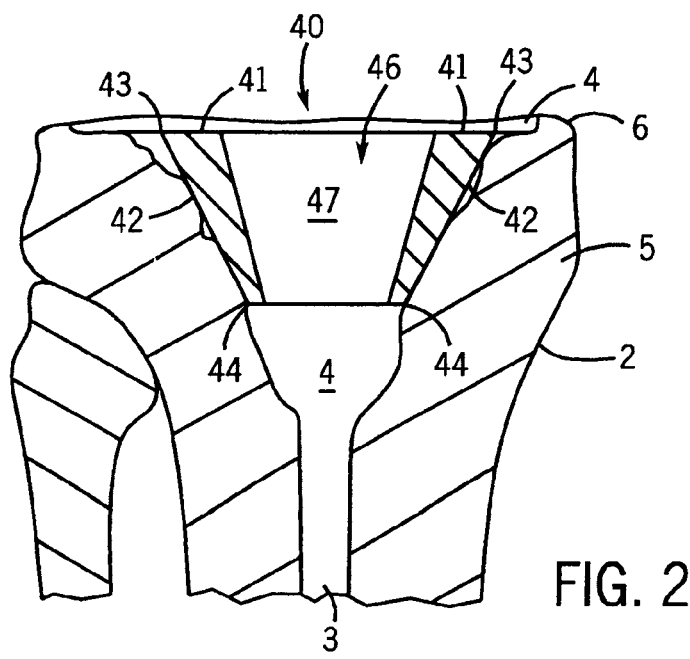
FIG. 2 is a cross-sectional view of the prosthetic implant support structure of FIG. 1 as placed in a tibia.
Figure 3:
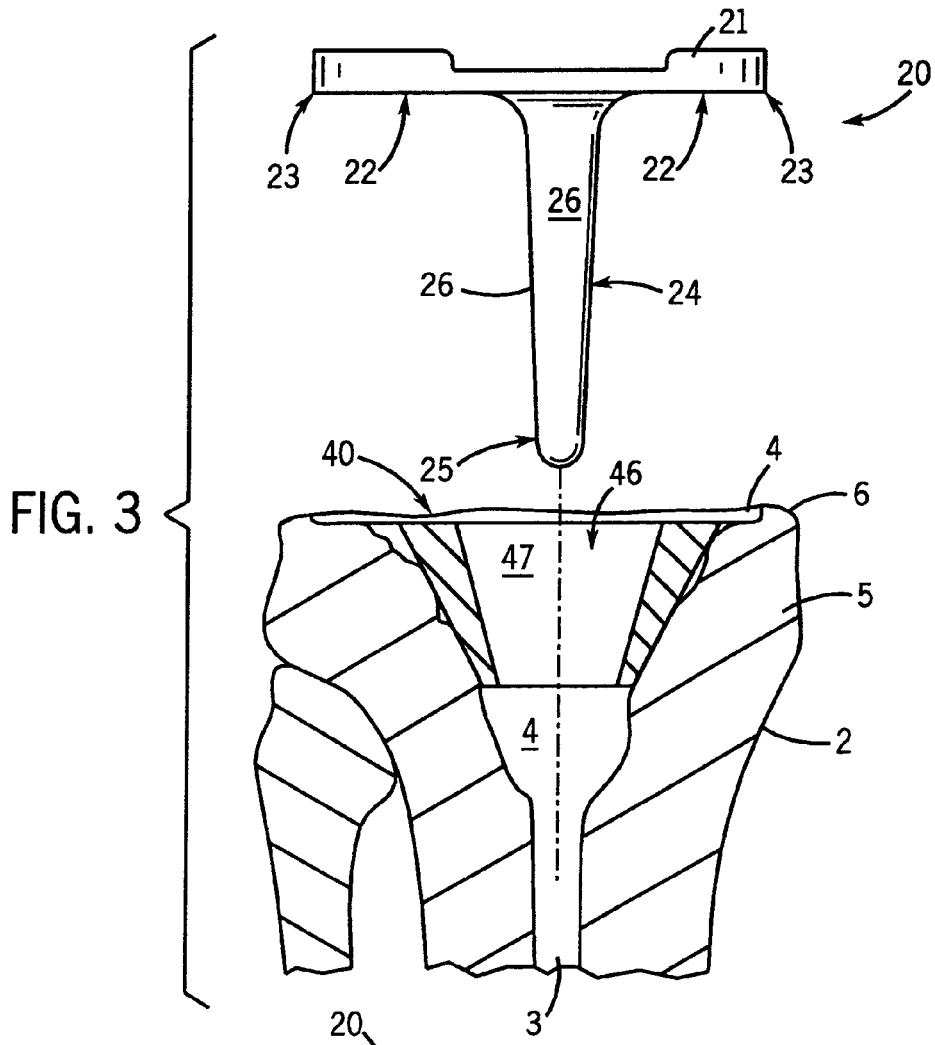
FIG. 3 is a side view of a prosthetic implant being placed in the prosthetic implant support structure in the tibia as shown in FIG. 2.

Looking first at FIGS. 1 to 4, there is shown a prosthetic system that includes a tibial implant 20 and a funnel shaped sleeve 40 that is secured to the inner surface 4 of the medullary canal (cavity) 3 of the end portion 5 of a tibia 2. The tibial implant 20, which is best shown in FIG. 3, has a body portion 21 and a stem 24 which extends outward from the body portion 21. The body portion 21 includes a bearing surface 22 that is typically affixed to the end surface 6 of the end portion 5 of the tibia. The outer limits of the bearing surface 22 define a perimeter 23. The stem 24 of the tibial implant 20 has a distal portion 25 and an outer surface 26. The tibial implant 20 is of conventional design and articulates with a femoral knee prosthesis (not shown) as is well known in the art.

Referring to FIG. 1, there is shown the tibia 2 and the funnel shaped sleeve 40 that supports the tibial implant 20 as will be described below. From FIG. 1, it can be seen that at the junction of the metaphysis and diaphysis of the tibia 2, there is a funnel shaped bone defect 7 which can be fashioned to provide a large surface area of bone. The funnel shaped sleeve 40 is impacted into the end portion 5 of the tibia 2 so that the external geometry of the funnel shaped sleeve 40 is firmly wedged into the metaphyseal-diaphyseal junction as shown in FIG. 2.

The funnel shaped sleeve 40 defines an axial access channel 46 that extends through the length of the funnel shaped sleeve 40. The funnel shaped sleeve 40 has a top end surface 41, an outer surface 42, and an inner surface 47 of the access channel 46. In the version of the funnel shaped sleeve 40 shown, the outer surface 42 of the funnel shaped sleeve 40 is sloped such that the length of a top end perimeter 43 of the funnel shaped sleeve 40 is greater than the length of a bottom end perimeter 44 at an opposite end of the funnel shaped sleeve 40. The inner surface 47 of the access channel 46 may be similarly sloped if desired. The funnel shaped sleeve 40 may be formed from a metal alloy such as titanium alloys (e.g., titanium-6-aluminum-4-vanadium), cobalt-chromium alloys, stainless steel alloys and tantalum alloys; nonresorbable ceramics such as aluminum oxide and zirconia; nonresorbable polymeric materials such as polyethylene; or composite materials such as carbon fiber-reinforced polymers (e.g., polysulfone). Preferably, the funnel shaped sleeve 40 is formed from a metal alloy.

The outer surface 42 of the funnel shaped sleeve 40 may be provided with a metallic texture coating which provides a textured surface so as to attain the desired fixation (by way of tissue ingrowth) between the funnel shaped sleeve 40 and the inner surface 4 of the medullary canal (cavity) 3 of the end portion 5 of the tibia 2 within which the funnel shaped sleeve 40 is implanted. The inner surface 47 of the access channel 46 of the funnel shaped sleeve 40 has a rough or corrugated surface finish to facilitate the interdigitation of bone cement. Likewise, the top end surface 41 of the funnel shaped sleeve 40 has a rough or corrugated surface finish to facilitate the interdigitation of bone cement. The funnel shaped sleeve 40 may have a variety of shapes and sizes, which vary by height, width and depth. A surgeon can use conventional measurement tools to select the height, width and depth of the funnel shaped sleeve 40.

Figure 4:
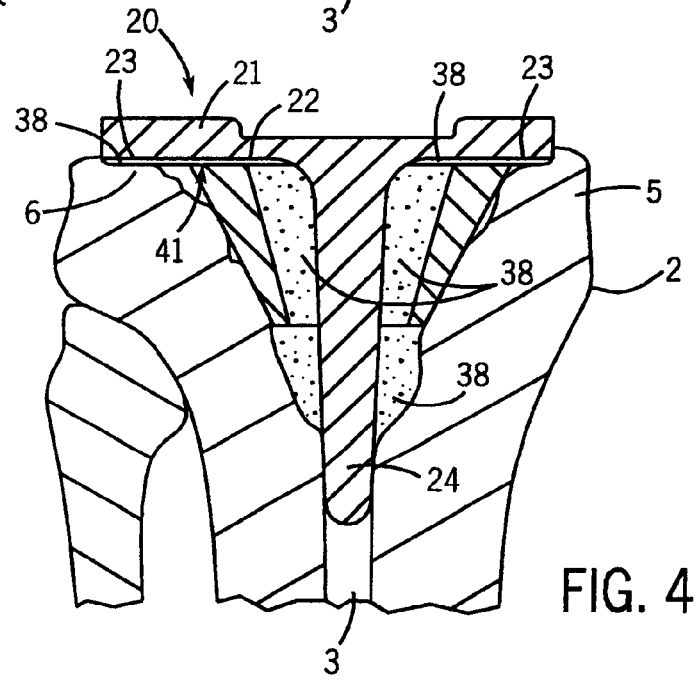
FIG. 4 is a cross-sectional view of the prosthetic implant as placed in the prosthetic support structure in the tibia as shown in FIG. 3.

The prosthetic system shown in FIGS. 1 to 4 may be implanted in a bone as follows. First, the end portion 5 of the tibia 2 is inspected and tools (such as a reamer) may be used to clean material out of the medullary canal (cavity) 3 or the bone defect 7 (if any). Once the medullary canal (cavity) 3 and the bone defect 7 have been prepared, the funnel shaped sleeve 40 is impacted into the end portion 5 of the tibia 2 so that the external geometry of the funnel shaped sleeve 40 is firmly wedged into the tibia 2. If desired, conventional bone cement such as an acrylic cement (e.g., polymethyl methacrylate) may be used to secure the outer surface 42 of the funnel shaped sleeve 40 to the inner surface 4 of the medullary canal (cavity) 3 of the end portion 5 of a tibia 2. Next, the stem 24 of the tibial implant 20 is moved into the access channel 46 of the funnel shaped sleeve 40. As shown in FIG. 4, at least a portion of the outer surface 26 of the stem 24 of the tibial implant 20 is secured to the inner surface 47 of the access channel 46 of the funnel shaped sleeve 40 with a suitable adhesive such as bone cement 38 (e.g., polymethyl methacrylate). Optionally, the distal portion 25 of the tibial implant 20 (which extends beyond the length of the funnel shaped sleeve 40) may be secured to the inner surface 4 of the medullary canal (cavity) 3 of the tibia 2 with a suitable adhesive such as bone cement 38 (e.g., polymethyl methacrylate).

Looking at FIG. 4 (which shows the tibial implant 20 and the funnel shaped sleeve 40 implanted in the tibia 2), several aspects of the invention can be described. For example, it can be seen that a portion of the bearing surface 22 of the tibial implant 20 is secured by cement 38 to the top end surface 41 of the funnel shaped sleeve 40 adjacent the end portion 5 of the tibia 2. The top end surface 41 of the funnel shaped sleeve 40 provides a rough or corrugated surface finish to facilitate the interdigitation of bone cement and provides an attachment surface for the tibial implant 20 where bone stock has been lost. Also, the region near the perimeter 23 of the bearing surface 22 of the tibial implant 20 is secured by cement 38 to the end surface 6 of the end portion 5 of the tibia 2. This provides for additional support for the tibial implant 20. The simultaneous attachment of the bearing surface 22 of the tibial implant 20 to the top end surface 41 of the funnel shaped sleeve 40 and to the end surface 6 of the end portion 5 of the tibia 2 is possible because the funnel shaped sleeve 40 is positioned in the cavity 3 of the tibia 2 such that the funnel shaped sleeve 40 does not extend beyond a plane defined by the end surface 6 of the end portion 5 of the tibia 2.

Because the funnel shaped sleeve 40 is not an integral component of the tibial implant 20, the funnel shaped sleeve 40 can be used with any stemmed prosthesis regardless of manufacturer or prosthetic design. Further, it should be noted that the example given in FIGS. 1 to 4 relates to use of the funnel shaped sleeve 40 in the proximal tibia; however, another common site where the funnel shaped sleeve 40 would be frequently used is the distal femur. Still other anatomic sites would include any joint that undergoes prosthetic arthroplasty when there is a significant metaphyseal bone deficiency.

In the presence of severe bone deficiency, the diaphyseal region of a bone is often deficient or absent and often requires the use of bone graft or unique prosthetic designs to achieve adequate prosthesis fixation during complex primary or revision knee and hip arthroplasty. As detailed above, the use of large structural allografts to restore bone stock requires a sophisticated bone banking system and is associated with the potential transmission of viral or bacterial pathogens. Furthermore, the difficulties with sizing and bone graft preparation are cumbersome and inexact. The advantages of minimizing disease transmission by minimizing use of allograft material and reduced operative times can be achieved with another prosthetic system according to the invention as shown in FIGS. 5 to 11. The prosthetic system allows for the insertion of a cylindrical porous sleeve into a large cavernous diaphyseal bone defect and also allows for the replacement of a segmental or complete diaphyseal bone deficiency.

Figures 10, 11:
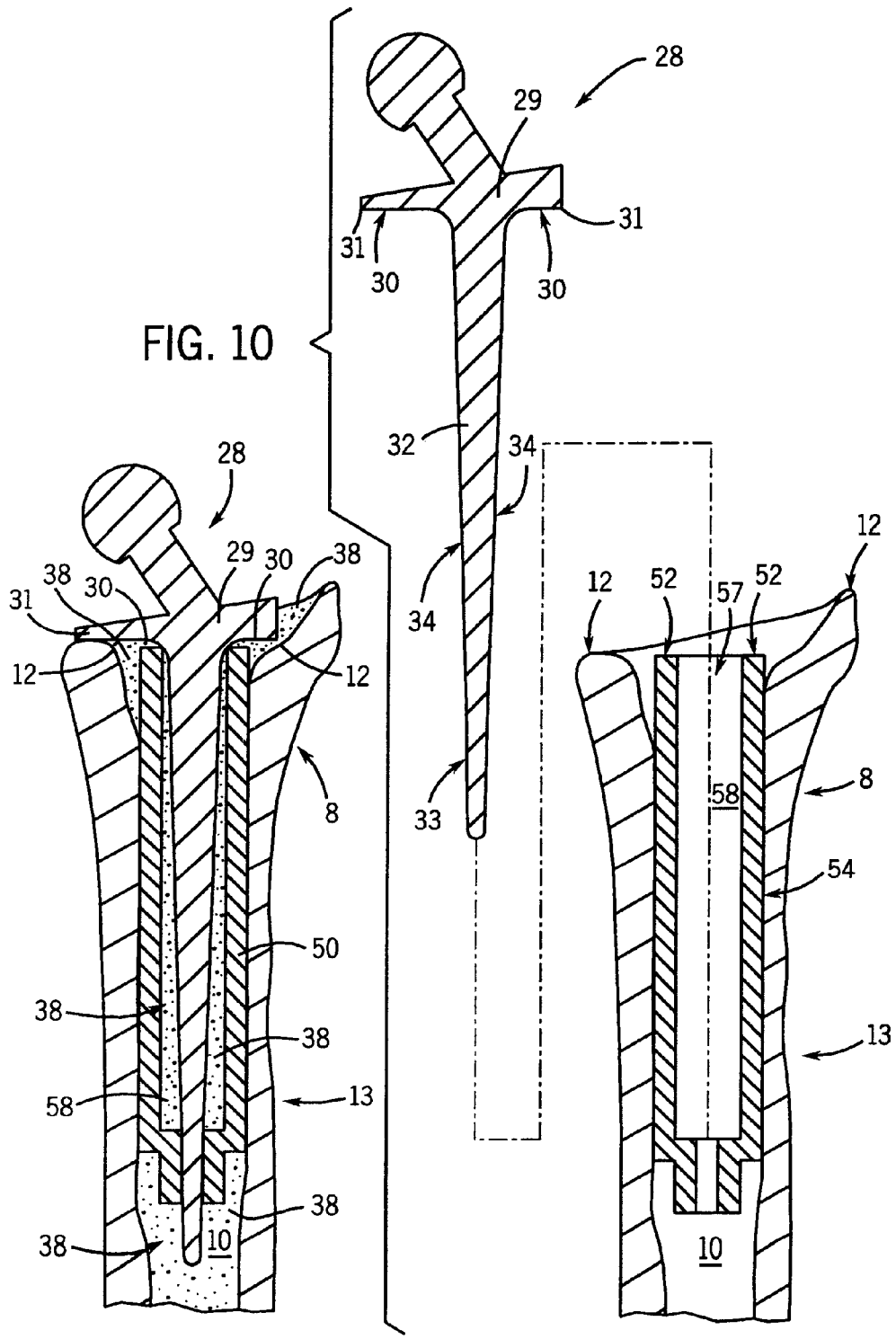
FIG. 10 is a cross-sectional view of a prosthetic implant being placed in the prosthetic support structure of FIG. 5 as placed in the femur as shown in FIG. 9.
FIG. 11 is a cross-sectional view of a prosthetic implant placed in the prosthetic support structure of FIG. 5 as placed in the femur as shown in FIG. 9.

Referring now to FIGS. 5 to 11, there is shown a prosthetic system that includes a femoral implant 28 and a cylindrically shaped sleeve 50 that is secured to the inner surface 10 of the medullary canal (cavity) 9 of a femur 8. The femoral implant 28, which is best shown in FIG. 10, has a body portion 29 and a stem 32 which extends outward from the body portion 29. The body portion 29 includes a bearing surface 30 that is typically affixed to the end surface 12 of the end portion 11 of the femur 8. The outer limits of the bearing surface 30 define a perimeter 31. The stem 32 of the femoral implant 28 has a distal portion 33 and an outer surface 34. The femoral implant 28 is of conventional design and is secured for movement within an acetabular cup (not shown) as is well known in the hip replacement art.

Referring to FIG. 8, there is shown the femur 8 and the cylindrical sleeve 50 that supports the femoral implant 28 as will be described below. From FIG. 8, it can be seen that at the diaphyseal region 13 of the femur 8, there is a bone defect. The cylindrical sleeve 50 is impacted into the cavity 9 of the femur 8 so that the external geometry of the cylindrical sleeve 50 is firmly wedged into the diaphyseal region 13 of the femur as shown in FIG. 9.

The cylindrical sleeve 50 defines an axial access channel 57 that extends through the length of the cylindrical sleeve 50. The cylindrical sleeve 50 has a top end surface 52, an outer surface 54, and an inner surface 58 of the access channel 57. The cylindrical sleeve 50 has a cylindrical upper section 51 having a first outside diameter and a cylindrical lower section 55 having a second outside diameter less than the first outside diameter. The access channel 57 may be cylindrical or optionally, the access channel 57 may be configured to accept various implant stem designs. For example, it can be seen from FIG. 6 that the access channel 57 in the upper section 51 of the cylindrical sleeve 50 has an approximately oval cross-section and from FIG. 7 that the access channel 57 in the lower section 55 of the cylindrical sleeve 50 has an approximately circular cross-section. The cylindrical sleeve 50 may be formed from a porous metal alloy such as titanium alloys (e.g., titanium-6-aluminum-4-vanadium), cobalt-chromium alloys, stainless steel alloys and tantalum alloys; nonresorbable porous ceramics such as aluminum oxide and zirconia; nonresorbable porous polymeric materials such as polyethylene; or porous composite materials such as carbon fiber-reinforced polymers (e.g., polysulfone). Preferably, the cylindrical sleeve 50 is formed from a porous metal alloy.

The outer surface 54 of the cylindrical sleeve 50 may also be provided with a metallic texture coating which provides a textured surface so as to attain the desired fixation (by way of tissue ingrowth) between the cylindrical sleeve 50 and the inner surface 10 of the medullary canal (cavity) 9 of the femur 8 within which the cylindrical sleeve 50 is implanted. The inner surface 58 of the access channel 57 of the cylindrical sleeve 50 has a rough or corrugated surface finish to facilitate the interdigitation of bone cement. Likewise, the top end surface 52 of the cylindrical sleeve 50 has a rough or corrugated surface finish to facilitate the interdigitation of bone cement. The cylindrical sleeve 50 may comprise any number of different sizes and lengths so that a surgeon is able to pick the appropriate sized sleeve for the patient after intraoperative assessment and thereby avoid difficulties of size mismatch and bone graft contouring. A surgeon can use conventional measurement tools to select the length and width of the cylindrical sleeve 50.

The prosthetic system shown in FIGS. 5 to 11 may be implanted in a bone as follows. First, the cavity 9 of the femur 8 is inspected and tools (such as a reamer) may be used to clean material out of the medullary canal (cavity) 9 or the bone defect (if any). Once the medullary canal (cavity) 9 and the bone defect have been prepared, the cylindrical sleeve 50 is impacted into the femur 2 so that the external geometry of the cylindrical sleeve 50 is firmly wedged into the femur 8. If desired, conventional bone cement such as an acrylic cement (e.g., polymethyl methacrylate) may be used to secure the outer surface 54 of the cylindrical sleeve 50 to the inner surface 10 of the medullary canal (cavity) 9 of the femur 8. Next, the stem 32 of the femoral implant 28 is moved into the access channel 57 of the cylindrical sleeve 50. As shown in FIG. 11, at least a portion of the outer surface 34 of the stem 32 of the femoral implant 28 is secured to the inner surface 58 of the access channel 57 of the cylindrical sleeve 50 with a suitable adhesive such as bone cement 38 (e.g., polymethyl methacrylate). Implant fixation within the sleeve 50 is achieved by cement interdigitation into the rough or corrugated surface finish of the inner surface 58 of the access channel 57 of the cylindrical sleeve 50 or into the porous structure of the sleeve. Optionally, the distal portion 33 of the femoral implant 28 (which extends beyond the length of the cylindrical sleeve 50) may be secured to the inner surface 10 of the medullary canal (cavity) 9 of the femur 8 with a suitable adhesive such as bone cement 38 (e.g., polymethyl methacrylate).

Looking at FIG. 11 (which shows the femoral implant 28 and the cylindrical sleeve 50 implanted in the femur 8), several aspects of the invention can be described. For example, it can be seen that a portion of the bearing surface 30 of the femoral implant 28 is secured by cement 38 to the top end surface 12 of the cylindrical sleeve 50 adjacent the end portion 11 of the femur 8. The top end surface 52 of the cylindrical sleeve 50 provides a rough or corrugated surface finish to facilitate the interdigitation of bone cement and provides an attachment surface for the femoral implant 28 where bone stock has been lost. Also, the region near the perimeter 31 of the bearing surface 30 of the femoral implant 28 is secured by cement 38 to the end surface 12 of the end portion 11 of the femur 8. This provides for additional support for the femoral implant 28. The simultaneous attachment of the bearing surface 30 of the femoral implant 28 to the top end surface 52 of the cylindrical sleeve 50 and to the end surface 12 of the end portion 11 of the femur 8 is possible because the cylindrical sleeve 50 is positioned in the cavity 9 of the femur 8 such that the cylindrical sleeve 50 does not extend beyond a plane defined by the end surface 12 of the end portion 11 of the femur 8.

Because the cylindrical sleeve 50 is not an integral component of the femoral implant 28, the cylindrical sleeve 50 can be used with any stemmed prosthesis regardless of manufacturer or prosthetic design. The sleeve can accommodate any number of prosthetic designs and achieves fixation to remaining host tissue by soft tissue or bone ingrowth. Further, it should be noted that the example given in FIGS. 5 to 11 relates to use of the cylindrical sleeve 50 in the proximal femur; however, another common site where the cylindrical sleeve 50 would be frequently used is the proximal tibia. Still other anatomic sites would include any joint that undergoes prosthetic arthroplasty when there is a significant diaphyseal bone deficiency.

Turning now to FIGS. 12 to 16, there is shown a yet another prosthetic system according to the invention that includes a tibial implant 20 and a periprosthetic support structure, indicated generally at 80, that is secured to the inner surface 4 of the medullary canal (cavity) 3 of the end portion 5 of a tibia 2. The tibial implant 20, which is shown in FIGS. 14 to 16, is identical to the tibial implant 20 that was described above with reference to FIGS. 1 to 4 and therefore will not be described again.

Figure 12:
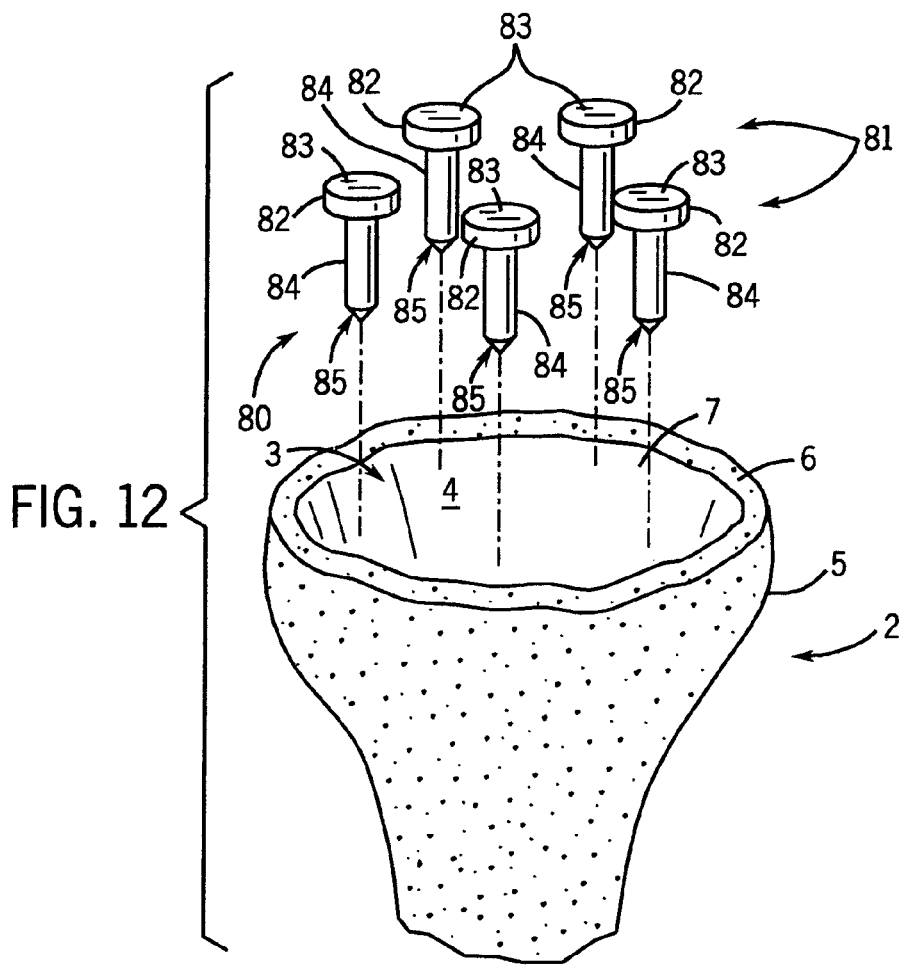
FIG. 12 is an exploded perspective view of yet another embodiment of a prosthetic implant support structure according to the invention being placed in a tibia.
Figure 13:
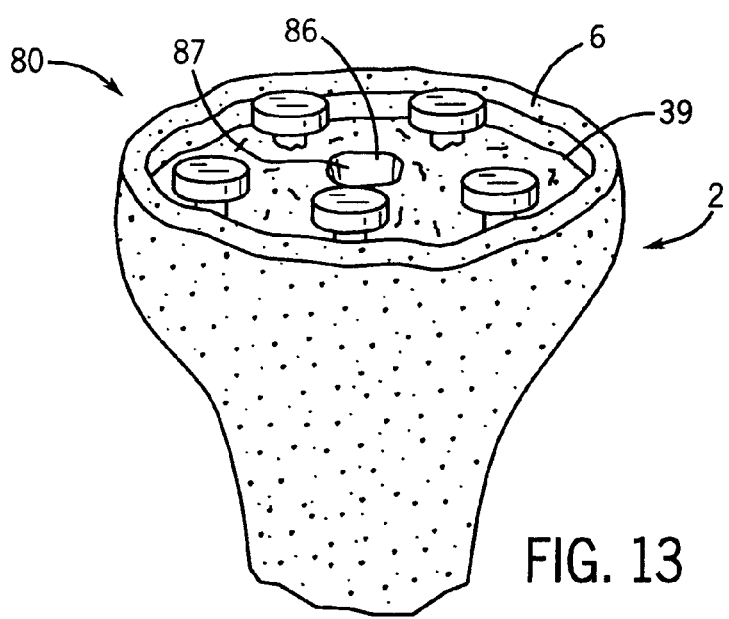
FIG. 13 is a perspective view of the prosthetic implant support structure of FIG. 12 as placed in a tibia.

Referring to FIG. 12, there is shown the tibia 2 and the periprosthetic support structure 80 that supports the tibial implant 20 as will be described below. From FIG. 12, it can be seen that at the junction of the metaphysis and diaphysis of the tibia 2, there is a funnel shaped bone defect 7 which can be fashioned to provide a large surface area of bone. The components of the periprosthetic support structure 80 are impacted into the end portion 5 of the tibia 2 so that the components of the periprosthetic support structure 80 are firmly wedged into the metaphyseal-diaphyseal junction as shown in FIG. 13.

The periprosthetic support structure 80 comprises a plurality of pedestals 81 that are impacted into or cemented to the inner surface 4 of the medullary canal (cavity) 3 of the end portion 5 of a tibia 2. Each pedestal 81 includes a flat disk shaped body section 82 having a top surface 83 and a stem section 84 extending substantially perpendicularly from the body section 82. The stem section 84 optionally includes a pointed end section 85 that facilitates impaction into the inner surface 4 of the medullary canal (cavity) 3 of the end portion 5 of a tibia 2. Each pedestal 81 may be formed from a metal alloy such as titanium alloys (e.g., titanium-6-aluminum-4-vanadium), cobalt-chromium alloys, stainless steel alloys and tantalum alloys; nonresorbable ceramics such as aluminum oxide and zirconia; nonresorbable polymeric materials such as polyethylene; or composite materials such as carbon fiber-reinforced polymers (e.g., polysulfone). Preferably, each pedestal 81 is formed from a metal alloy. The outer surfaces of each pedestal 81 (including the top surface 83) may be provided with a rough or corrugated surface finish to facilitate the interdigitation of bone cement. The body section 82 of each pedestal 80 may have a variety of shapes and sizes as long as there exists a generally flat portion on part of the top surface. The stem section 84 of each pedestal 81 may also have various lengths and widths. A surgeon can use conventional measurement tools to select the dimensions of each pedestal 81.

The pedestals 81 may be implanted in a bone as follows to form the periprosthetic support structure 80. First, the end portion 5 of the tibia 2 is inspected and tools (such as a reamer) may be used to clean material out of the medullary canal (cavity) 3 or the bone defect 7 (if any). Once the medullary canal (cavity) 3 and the bone defect 7 have been prepared, the stem section 84 of each pedestal 81 is impacted into or cemented onto the end portion 5 of the tibia 2 to form the periprosthetic support structure 80. The pedestals 81 may be arranged in any configuration; however, it is preferred that the pedestals 81 are arranged in the circular arrangement shown in FIGS. 13 and 14. The circular arrangement of the pedestals 81 creates an access channel that extends through the length of the periprosthetic support structure 80. Optionally, the periprosthetic support structure 80 may include bone graft material 39 that is placed around the pedestals 81 to form an access channel 86 having an inner surface 87 as shown in FIGS. 13 and 14. The bone graft material 39 may selected from known bone graft materials and may include crushed bone (cancellous and cortical), or a combination of these and synthetic biocompatible materials. As used herein, "bone graft" shall mean materials made up entirely of natural materials, entirely of synthetic biocompatible materials, or any combination of these materials.

After the periprosthetic support structure 80 is formed in a bone, the stem 24 of the tibial implant 20 may be moved into the access channel 86 of the periprosthetic support structure 80. As shown in FIG. 16, at least a portion of the outer surface 26 of the stem 24 of the tibial implant 20 is secured to the inner surface 87 of the access channel 86 of the periprosthetic support structure 80 with a suitable adhesive such as bone cement 38 (e.g., polymethyl methacrylate). Optionally, the distal portion 25 of the tibial implant 20 (which extends beyond the length of the periprosthetic support structure 80) may be secured to the inner surface 4 of the medullary canal (cavity) 3 of the tibia 2 with a suitable adhesive such as bone cement 38 (e.g., polymethyl methacrylate).

Looking at FIGS. 15 and 16 (which show the tibial implant 20 and the periprosthetic support structure 80 implanted in the tibia 2), several aspects of the invention can be described. For example, it can be seen that a portion of the bearing surface 22 of the tibial implant 20 is secured by cement 38 to the top surface 83 of each pedestal 81 of the periprosthetic support structure 80 adjacent the end portion 5 of the tibia 2. The top end surface 83 of each pedestal 81 of the periprosthetic support structure 80 provides a rough or corrugated surface finish to facilitate the interdigitation of bone cement and provides an attachment surface for the tibial implant 20 where bone stock has been lost. Also, the region near the perimeter 23 of the bearing surface 22 of the tibial implant 20 is secured by cement 38 to the end surface 6 of the end portion 5 of the tibia 2. This provides for additional support for the tibial implant 20. The simultaneous attachment of the bearing surface 22 of the tibial implant 20 to the top end surface 83 of each pedestal 81 of the periprosthetic support structure 80 and to the end surface 6 of the end portion 5 of the tibia 2 is possible because the periprosthetic support structure 80 is positioned in the cavity 3 of the tibia 2 such that the periprosthetic support structure 80 does not extend beyond a plane defined by the end surface 6 of the end portion 5 of the tibia 2.

Because the periprosthetic support structure 80 is not an integral component of the tibial implant 20, the periprosthetic support structure 80 can be used with any stemmed prosthesis regardless of manufacturer or prosthetic design. Further, it should be noted that the example given in FIGS. 12 to 16 relates to use of the periprosthetic support structure 80 in the proximal tibia; however, another common site where the periprosthetic support structure 80 would be frequently used is the distal femur. Still other anatomic sites would include any joint that undergoes prosthetic arthroplasty when there is a significant metaphyseal bone deficiency.

Figure 17:
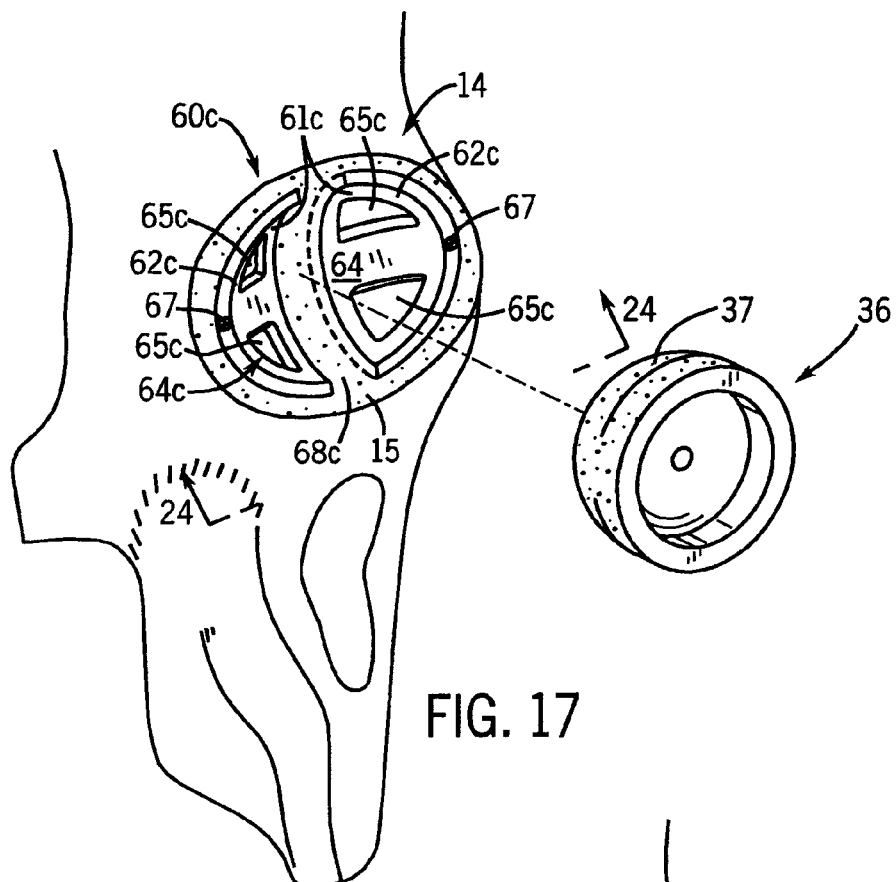
FIG. 17 is an exploded perspective view of an acetabular cup of a hip prosthesis being placed in still another embodiment of a prosthetic implant support structure according to the invention secured in the acetabular cavity of a hip.
Figure 24:
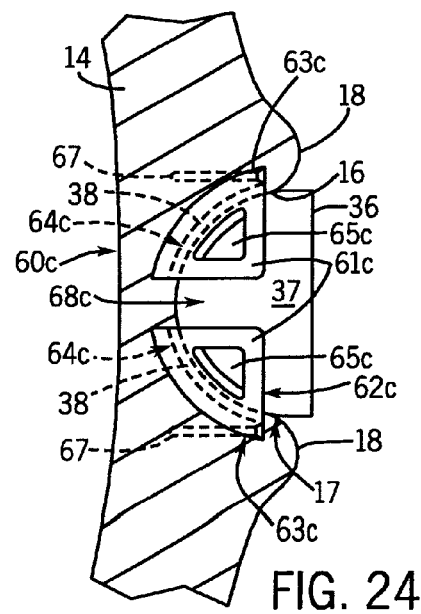
FIG. 24 is a cross-sectional view of an acetabular cup of a hip prosthesis placed in the prosthetic implant support structure of FIG. 17 taken along line 24-24 of FIG. 17.

Referring now to FIGS. 17 and 24, there is shown another prosthetic system according to the invention that includes an acetabular cup implant 36 having an outer surface 37 and a periprosthetic support structure, indicated generally at 60c, that is secured to the inner surface 16 of the acetabular cavity 15 of a hip bone 14. The periprosthetic support structure 60c comprises two support components 61c having a configuration approximating a quarter of a sphere. The support components 61c of the periprosthetic support structure 60c are impacted, screwed or cemented into the inner surface 16 of the acetabular cavity 15 of a hip bone 14 in a spaced apart relationship.

Each support component 61c may be formed from a metal alloy such as titanium alloys (e.g., titanium-6-aluminum-4-vanadium), cobalt-chromium alloys, stainless steel alloys and tantalum alloys; nonresorbable ceramics such as aluminum oxide and zirconia; nonresorbable polymeric materials such as polyethylene; or composite materials such as carbon fiber-reinforced polymers (e.g., polysulfone). Preferably, each support component 61c is formed from a metal alloy.

The outer surface 63c of each support component 61c may also be provided with a metallic texture coating which provides a textured surface so as to attain the desired fixation (by way of tissue ingrowth) between each support component 61c and the inner surface 16 of the acetabular cavity 15 of a hip bone 14 within which each support component 61c is implanted. The inner surface 64c of each support component 61c has a rough or corrugated surface finish to facilitate the interdigitation of bone cement. Likewise, the top end surface 62c of each support component 61c has a rough or corrugated surface finish to facilitate the interdigitation of bone cement. Each support component 61c also has fenestrations 65c which can be filled with bone graft material (e.g., morselized cancellous bone).

Each support component 61c may comprise any number of different heights, widths and depths so that a surgeon is able to pick the appropriate sized support component for the patient after intraoperative assessment and thereby avoid difficulties of size mismatch and bone graft contouring. A surgeon can use conventional measurement tools to select the size of each support component 61c. The size, position and orientation of each support component 61c and the use of supplemental screw fixation for each support component 61c is dependent on the size and location of the defects in the host bone as well as the quality of the bone that remains.

The support components 61c may be implanted in a bone as follows to form the periprosthetic support structure 60c. First, the acetabular cavity 15 of the hip bone 14 is inspected and tools (such as a reamer) may be used to clean material out of the acetabular cavity 15. Once the acetabular cavity 15 has been prepared, each support component 61c is impacted into or cemented onto the end portion 17 of the acetabular cavity 15 of the hip bone 14 in spaced apart relationship to form the periprosthetic support structure 60c. Preferably, each support component 61c is not cemented to the hip bone and therefore is available for bone ingrowth into the textured outer surface 63c of the support component 61c. The support components 61c shown in FIGS. 17 and 24 are also screwed into the hip bone 14 using screws 67 (shown in phantom in FIG. 24). The support components 61c may be arranged in any configuration that creates an access channel 68c that extends through the length of the periprosthetic support structure 60c. Preferably, the support components 61c are arranged to form a substantially hemispherical support structure. It can be seen that placement of the support components 61c precedes placement of any prosthetic joint components.

After the periprosthetic support structure 60c is constructed in a bone, the acetabular cup implant 36 may be placed into the access channel 68c of the periprosthetic support structure 60c. Placement can occur either during the same operative procedure as support component 61c placement or can be performed later once bone union to the support components 61c has occurred. In either instance, the acetabular cup implant 36 would be placed only after the acetabulum had been reconstructed using the support structure 60c. As shown in FIG. 24, at least a portion of the outer surface 37 of the acetabular cup implant 36 is secured to the inner surface 64c (shown in phantom) of the access channel 68c of the periprosthetic support structure 60c with a suitable adhesive such as bone cement 38 (e.g., polymethyl methacrylate). It can be seen that the periprosthetic support structure 60c does not extend beyond a plane defined by the end surface 18 of the end portion 17 of the hip bone 14.

Because the periprosthetic support structure 60c is not an integral component of the acetabular cup implant 36, the periprosthetic support structure 60c can be used with any acetabular cup implant 36 regardless of manufacturer or prosthetic design. Further, it should be noted that the example given in FIGS. 17 and 24 relates to use of the periprosthetic support structure 60c in the acetabular cavity of a hip bone; however, other common sites where the periprosthetic support structure 60c would be frequently used include the tibia and femur. Still other anatomic sites would include any joint that undergoes prosthetic arthroplasty when there is a significant metaphyseal bone deficiency.

Figure 18:
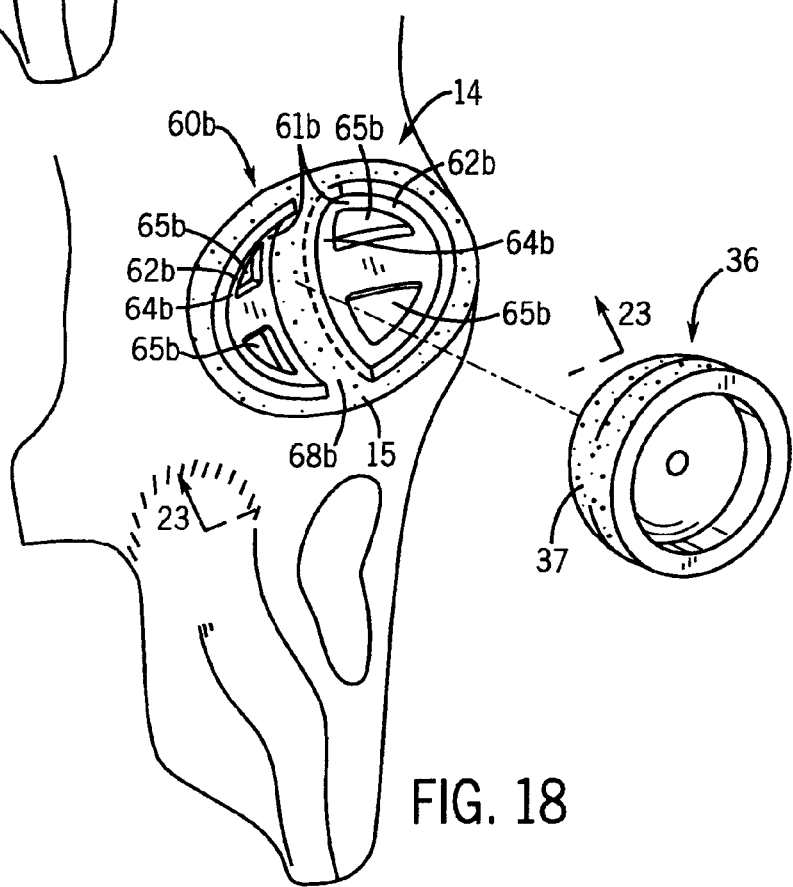
FIG. 18 is an exploded perspective view of an acetabular cup of a hip prosthesis being placed in a further embodiment of a prosthetic implant support structure according to the invention secured in the acetabular cavity of a hip.
Figure 23:
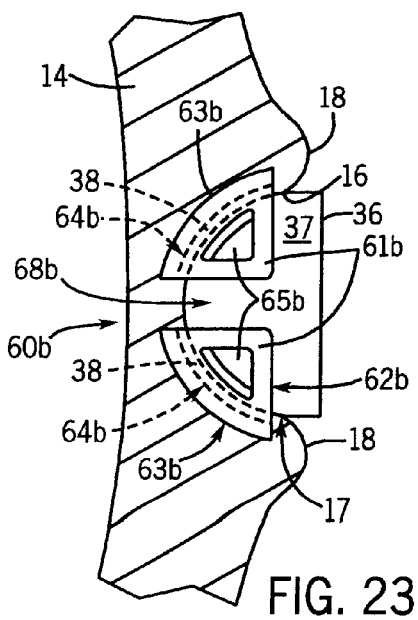
FIG. 23 is a cross-sectional view of an acetabular cup of a hip prosthesis placed in the prosthetic implant support structure of FIG. 18 taken along line 23-23 of FIG. 18.

Referring now to FIGS. 18 and 23, there is shown yet another prosthetic system according to the invention that includes an acetabular cup implant 36 having an outer surface 37 and a periprosthetic support structure, indicated generally at 60b, that is secured to the inner surface 16 of the acetabular cavity 15 of a hip bone 14. The periprosthetic support structure 60b comprises two support components 61b having a configuration approximating a quarter of a sphere. The support components 61b of the periprosthetic support structure 60b are impacted and/or cemented into the inner surface 16 of the acetabular cavity 15 of a hip bone 14 in a spaced apart relationship.

Each support component 61b may be formed from a metal alloy such as titanium alloys (e.g., titanium-6-aluminum-4-vanadium), cobalt-chromium alloys, stainless steel alloys and tantalum alloys; nonresorbable ceramics such as aluminum oxide and zirconia; nonresorbable polymeric materials such as polyethylene; or composite materials such as carbon fiber-reinforced polymers (e.g., polysulfone). Preferably, each support component 61b is formed from a metal alloy.

The outer surface 63b of each support component 61b may also be provided with a metallic texture coating which provides a textured surface so as to attain the desired fixation (by way of tissue ingrowth) between each support component 61b and the inner surface 16 of the acetabular cavity 15 of a hip bone 14 within which each support component 61b is implanted. The inner surface 64b of each support component 61b has a rough or corrugated surface finish to facilitate the interdigitation of bone cement. Likewise, the top end surface 62b of each support component 61b has a rough or corrugated surface finish to facilitate the interdigitation of bone cement. Each support component 61b also has fenestrations 65b which can be filled with bone graft material (e.g., morselized cancellous bone).

Each support component 61b may comprise any number of different heights, widths and depths so that a surgeon is able to pick the appropriate sized support component for the patient after intraoperative assessment and thereby avoid difficulties of size mismatch and bone graft contouring. A surgeon can use conventional measurement tools to select the size of each support component 61b. The size, position and orientation of each support component 61b is dependent on the size and location of the defects in the host bone as well as the quality of the bone that remains.

The support components 61b may be implanted in a bone as follows to form the periprosthetic support structure 60b. First, the acetabular cavity 15 of the hip bone 14 is inspected and tools (such as a reamer) may be used to clean material out of the acetabular cavity 15. Once the acetabular cavity 15 has been prepared, each support component 61b is impacted into or cemented onto the end portion 17 of the acetabular cavity 15 of the hip bone 14 in spaced apart relationship to form the periprosthetic support structure 60b. Preferably, each support component 61b is not cemented to the hip bone and therefore is available for bone ingrowth into the textured outer surface 63b of the support component 61b. The support components 61b may be arranged in any configuration that creates an access channel 68b that extends through the length of the periprosthetic support structure 60b. Preferably, the support components 61b are arranged to form a substantially hemispherical support structure. It can be seen that placement of the support components 61b precedes placement of any prosthetic joint components.

After the periprosthetic support structure 60b is constructed in a bone, the acetabular cup implant 36 may be placed into the access channel 68b of the periprosthetic support structure 60b. Placement can occur either during the same operative procedure as support component 61b placement or can be performed later once bone union to the support components 61b has occurred. In either instance, the acetabular cup implant 36 would be placed only after the acetabulum had been reconstructed using the support structure 60b. As shown in FIG. 23, at least a portion of the outer surface 37 of the acetabular cup implant 36 is secured to the inner surface 64b (shown in phantom) of the access channel 68b of the periprosthetic support structure 60b with a suitable adhesive such as bone cement 38 (e.g., polymethyl methacrylate). It can be seen that the periprosthetic support structure 60b does not extend beyond a plane defined by the end surface 18 of the end portion 17 of the hip bone 14.

Because the periprosthetic support structure 60b is not an integral component of the acetabular cup implant 36, the periprosthetic support structure 60b can be used with any acetabular cup implant 36 regardless of manufacturer or prosthetic design. Further, it should be noted that the example given in FIGS. 18 and 23 relates to use of the periprosthetic support structure 60b in the acetabular cavity of a hip bone; however, other common sites where the periprosthetic support structure 60b would be frequently used include the tibia and femur. Still other anatomic sites would include any joint that undergoes prosthetic arthroplasty when there is a significant metaphyseal bone deficiency.

Figure 19:
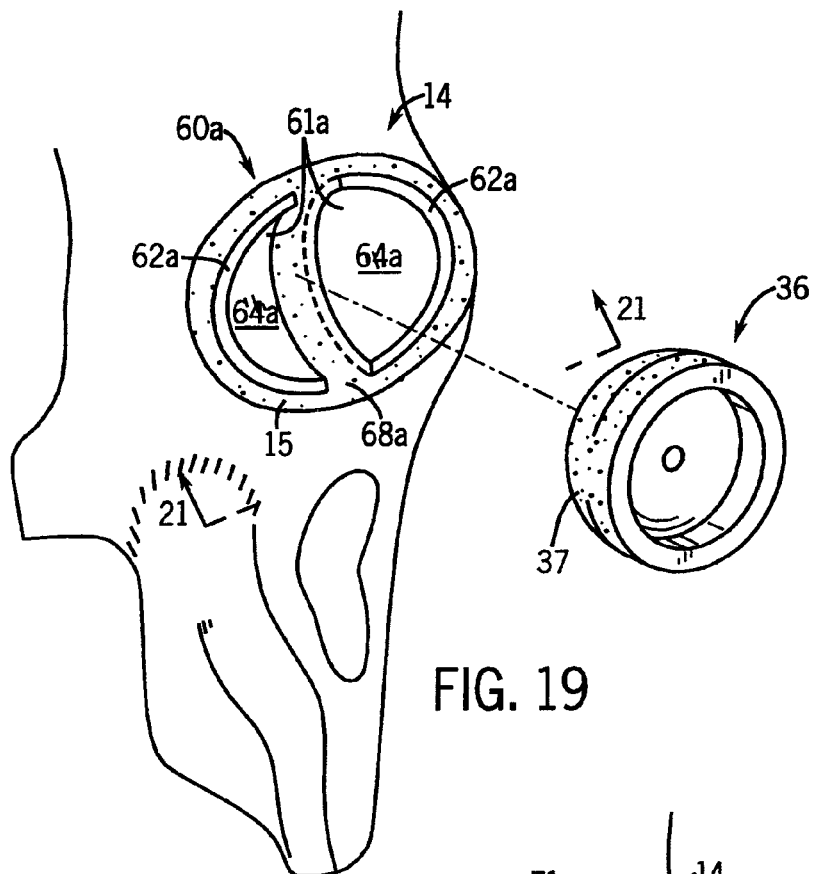
FIG. 19 is an exploded perspective view of an acetabular cup of a hip prosthesis being placed in yet another embodiment of a prosthetic implant support structure according to the invention secured in the acetabular cavity of a hip.
Figure 21:
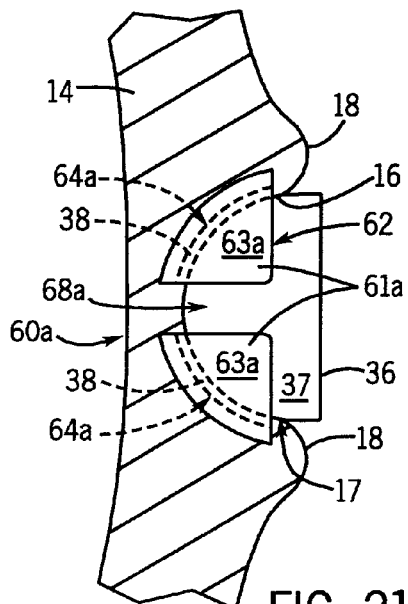
FIG. 21 is a cross-sectional view of an acetabular cup of a hip prosthesis placed in the prosthetic implant support structure of FIG. 19 taken along line 21-21 of FIG. 19.

Referring now to FIGS. 19 and 21, there is shown yet another prosthetic system according to the invention that includes an acetabular cup implant 36 having an outer surface 37 and a periprosthetic support structure, indicated generally at 60a, that is secured to the inner surface 16 of the acetabular cavity 15 of a hip bone 14. The periprosthetic support structure 60a comprises two support components 61a having a configuration approximating a quarter of a sphere. The support components 61a of the periprosthetic support structure 60a are impacted and/or cemented into the inner surface 16 of the acetabular cavity 15 of a hip bone 14 in a spaced apart relationship.

Each support component 61a may be formed from a metal alloy such as titanium alloys (e.g., titanium-6-aluminum-4-vanadium), cobalt-chromium alloys, stainless steel alloys and tantalum alloys; nonresorbable ceramics such as aluminum oxide and zirconia; nonresorbable polymeric materials such as polyethylene; or composite materials such as carbon fiber-reinforced polymers (e.g., polysulfone). Preferably, each support component 61a is formed from a metal alloy.

The outer surface 63a of each support component 61a may also be provided with a metallic texture coating which provides a textured surface so as to attain the desired fixation (by way of tissue ingrowth) between each support component 61a and the inner surface 16 of the acetabular cavity 15 of a hip bone 14 within which each support component 61a is implanted. The inner surface 64a of each support component 61a has a rough or corrugated surface finish to facilitate the interdigitation of bone cement. Likewise, the top end surface 62a of each support component 61a has a rough or corrugated surface finish to facilitate the interdigitation of bone cement.

Each support component 61a may comprise any number of different heights, widths and depths so that a surgeon is able to pick the appropriate sized support component for the patient after intraoperative assessment and thereby avoid difficulties of size mismatch and bone graft contouring. A surgeon can use conventional measurement tools to select the size of each support component 61a. The size, position and orientation of each support component 61a is dependent on the size and location of the defects in the host bone as well as the quality of the bone that remains.

The support components 61a may be implanted in a bone as follows to form the periprosthetic support structure 60a. First, the acetabular cavity 15 of the hip bone 14 is inspected and tools (such as a reamer) may be used to clean material out of the acetabular cavity 15. Once the acetabular cavity 15 has been prepared, each support component 61a is impacted into or cemented onto the end portion 17 of the acetabular cavity 15 of the hip bone 14 in spaced apart relationship to form the periprosthetic support structure 60a. Preferably, each support component 61a is not cemented to the hip bone and therefore is available for bone ingrowth into the textured outer surface 63a of the support component 61a. The support components 61a may be arranged in any configuration that creates an access channel 68a that extends through the length of the periprosthetic support structure 60a. Preferably, the support components 61a are arranged to form a substantially hemispherical support structure. It can be seen that placement of the support components 61a precedes placement of any prosthetic joint components.

After the periprosthetic support structure 60a is constructed in a bone, the acetabular cup implant 36 may be placed into the access channel 68a of the periprosthetic support structure 60a. Placement can occur either during the same operative procedure as support component 61a placement or can be performed later once bone union to the support components 61a has occurred. In either instance, the acetabular cup implant 36 would be placed only after the acetabulum had been reconstructed using the support structure 60a. As shown in FIG. 21, at least a portion of the outer surface 37 of the acetabular cup implant 36 is secured to the inner surface 64a (shown in phantom) of the access channel 68a of the periprosthetic support structure 60a with a suitable adhesive such as bone cement 38 (e.g., polymethyl methacrylate). It can be seen that the periprosthetic support structure 60a does not extend beyond a plane defined by the end surface 18 of the end portion 17 of the hip bone 14.

Because the periprosthetic support structure 60a is not an integral component of the acetabular cup implant 36, the periprosthetic support structure 60a can be used with any acetabular cup implant 36 regardless of manufacturer or prosthetic design. Further, it should be noted that the example given in FIGS. 19 and 21 relates to use of the periprosthetic support structure 60a in the acetabular cavity of a hip bone; however, other common sites where the periprosthetic support structure 60a would be frequently used include the tibia and femur. Still other anatomic sites would include any joint that undergoes prosthetic arthroplasty when there is a significant metaphyseal bone deficiency.

Figure 20:
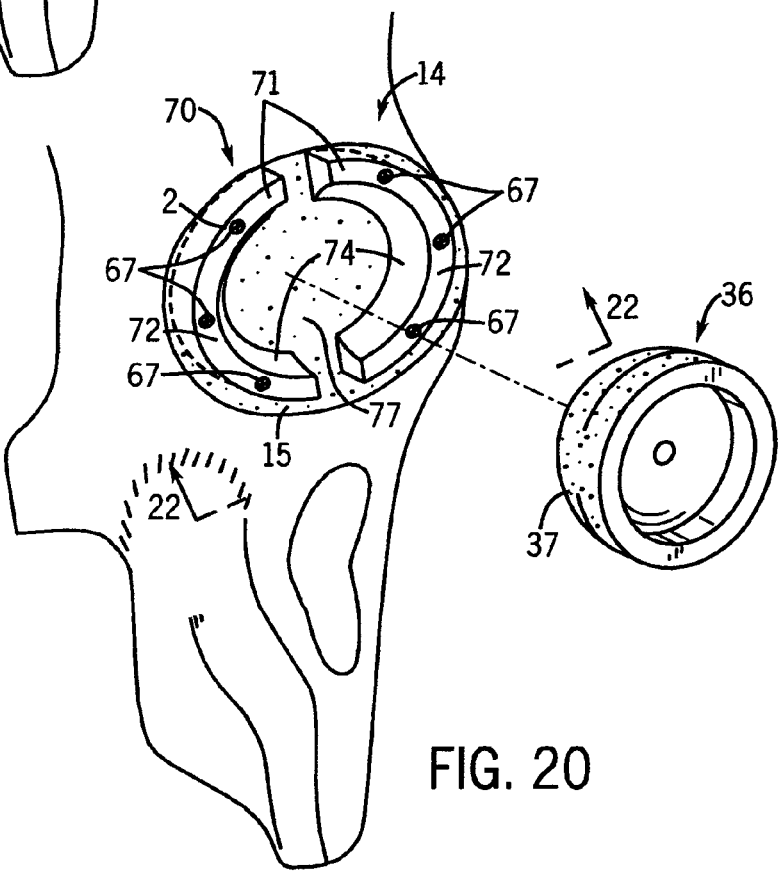
FIG. 20 is an exploded perspective view of an acetabular cup of a hip prosthesis being placed in still another embodiment of a prosthetic implant support structure according to the invention secured in the acetabular cavity of a hip.
Figure 22:
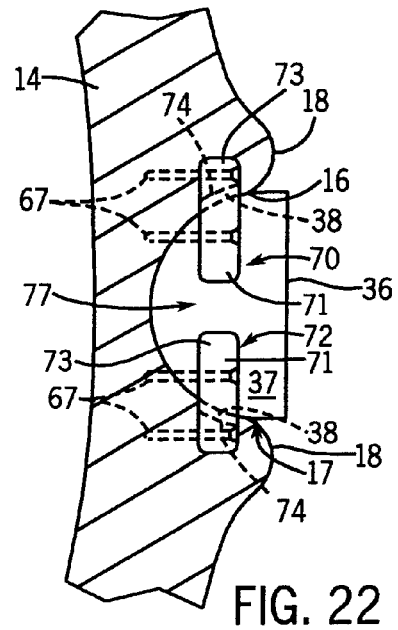
FIG. 22 is a cross-sectional view of an acetabular cup of a hip prosthesis placed in the prosthetic implant support structure of FIG. 20 taken along line 22-22 of FIG. 20.

Referring now to FIGS. 20 and 22, there is shown yet another prosthetic system according to the invention that includes an acetabular cup implant 36 having an outer surface 37 and a periprosthetic support structure, indicated generally at 70, that is secured to the inner surface 16 of the acetabular cavity 15 of a hip bone 14. The periprosthetic support structure 70 comprises two support components 71 having a configuration approximating a boomerang shape. The support components 71 of the periprosthetic support structure 70 are impacted, screwed and/or cemented into the inner surface 16 of the acetabular cavity 15 of a hip bone 14 in a spaced apart relationship.

Each support component 71 may be formed from a metal alloy such as titanium alloys (e.g., titanium-6-aluminum-4-vanadium), cobalt-chromium alloys, stainless steel alloys and tantalum alloys; nonresorbable ceramics such as aluminum oxide and zirconia; nonresorbable polymeric materials such as polyethylene; or composite materials such as carbon fiber-reinforced polymers (e.g., polysulfone). Preferably, each support component 71 is formed from a metal alloy.

The outer surface 73 of each support component 71 may also be provided with a metallic texture coating which provides a textured surface so as to attain the desired fixation (by way of tissue ingrowth) between each support component 71 and the inner surface 16 of the acetabular cavity 15 of a hip bone 14 within which each support component 71 is implanted. The inner surface 74 of each support component 71 has a rough or corrugated surface finish to facilitate the interdigitation of bone cement. Likewise, the top end surface 72 of each support component 71 has a rough or corrugated surface finish to facilitate the interdigitation of bone cement. Each support component 71 may comprise any number of different heights, widths and depths so that a surgeon is able to pick the appropriate sized support component for the patient after intraoperative assessment and thereby avoid difficulties of size mismatch and bone graft contouring. A surgeon can use conventional measurement tools to select the size of each support component 71.

The support components 71 may be implanted in a bone as follows to form the periprosthetic support structure 70. First, the acetabular cavity 15 of the hip bone 14 is inspected and tools (such as a reamer) may be used to clean material out of the acetabular cavity 15. Once the acetabular cavity 15 has been prepared, each support component 71 is placed into, impacted into, or cemented onto the end portion 17 of the acetabular cavity 15 of the hip bone 14 in spaced apart relationship to form the periprosthetic support structure 70. The support components 71 shown in FIGS. 20 and 22 are screwed into the hip bone 14 using screws 67 (shown in phantom in FIG. 22). The support components 71 may be arranged in any configuration that creates an access channel 77 that extends through the length of the periprosthetic support structure 70. The size, position and orientation of each support component 71 is dependent on the size and location of the defects in the host bone as well as the quality of the bone that remains.

After the periprosthetic support structure 70 is constructed in a bone, the acetabular cup implant 36 may be placed into the access channel 77 of the periprosthetic support structure 70. Placement can occur either during the same operative procedure as support component 71 placement or can be performed later once bone union to the support components 71 has occurred. In either instance, the acetabular cup implant 36 would be placed only after the acetabulum had been reconstructed using the support structure 70. As shown in FIG. 22, at least a portion of the outer surface 37 of the acetabular cup implant 36 is secured to the inner surface 74 (shown in phantom) of the access channel 77 of the periprosthetic support structure 70 with a suitable adhesive such as bone cement 38 (e.g., polymethyl methacrylate). It can be seen that the periprosthetic support structure 70 does not extend beyond a plane defined by the end surface 18 of the end portion 17 of the hip bone 14.

Because the periprosthetic support structure 70 is not an integral component of the acetabular cup implant 36, the periprosthetic support structure 70 can be used with any acetabular cup implant 36 regardless of manufacturer or prosthetic design. Further, it should be noted that the example given in FIGS. 20 and 22 relates to use of the periprosthetic support structure 70 in the acetabular cavity of a hip bone; however, other common sites where the periprosthetic support structure 70 would be frequently used include the tibia and femur. Still other anatomic sites would include any joint that undergoes prosthetic arthroplasty when there is a significant metaphyseal bone deficiency.

Therefore, the present invention provides prosthetic implant support structures that solve the problems associated with the loss of strong bone stock near a joint being replaced with a prosthesis. The described prosthetic implant support structures do not rely on the use of large amounts of bone graft or cumbersome bone graft delivery devices. The prosthetic implant support structures can eliminate the need to cement the distal portion of the stem of an implant to the inner surface of a bone cavity and can be used with a wide variety of prosthetic implants obtained from any number of different implant manufacturers. Furthermore, the described prosthetic implant system can optimize implant support on intact host bone with minimal removal of residual host bone and encourages bone ingrowth and attachment over as large a surface area as possible.

While the implantation of tibial, femoral, and acetabular prostheses has been illustrated and described herein, one skilled in the art will appreciate that the present invention can be practiced by other than the described embodiments, which have been presented for purposes of illustration and not of limitation. For instance, the methods and prostheses according to the invention can be used in the repair of any bone or in connection with the implantation of prosthetic devices at or in any bone in the body. Accordingly, the scope of the appended claims should not be limited to the description of the embodiments contained herein.

What is claimed is:

1. A prosthetic system for implantation in a cavity in an end of a bone, the prosthetic system comprising:
    a prosthetic implant including a stem component;
    a hollow sleeve formed separately from said stem component for subsequent connection to said stem component, said hollow sleeve formed with a porous material and capable of being impacted into the cavity in the end of the bone for firmly wedging the hollow sleeve in the cavity prior to connecting said hollow sleeve to said stem component, wherein said porous material is a bone ingrowth-receptive material with a porous structure for encouraging bone ingrowth into the hollow sleeve, said hollow sleeve including an axial channel that extends through the length of the hollow sleeve for accommodating said stem component, wherein said stem component is received in the axial channel so as to leave an annular gap between an outer surface of the stem component and an interior surface of the hollow sleeve that is situated along said axial channel; and
    an adhesive located within said annular gap and interdigitating into said porous structure for securing said stem component in said axial channel.

2. The prosthetic system of claim 1, wherein said hollow sleeve includes an exterior surface.

3. The prosthetic system of claim 1, wherein a distal end of said stem component protrudes from said axial channel so as to extend beyond said hollow sleeve.

4. The prosthetic system of claim 1, wherein said interior surface of the hollow sleeve includes a textured surface.

5. The prosthetic system of claim 1, wherein said interior surface of the hollow sleeve includes a corrugated surface.

6. A prosthetic system for implantation in a cavity in an end of a bone, the prosthetic system comprising:
    a prosthetic implant including a stem component; and
    a hollow sleeve formed separately from said stem component for subsequent connection to said stem component, said hollow sleeve formed with a porous material and capable of being impacted into the cavity in the end of the bone for firmly wedging the hollow sleeve in the cavity prior to connecting said hollow sleeve to said stem component, wherein said porous material is a bone ingrowth-receptive material with a porous structure for encouraging bone ingrowth into the hollow sleeve, said hollow sleeve including an exterior surface and an interior surface with said interior surface situated along an axial channel that extends through the length of the hollow sleeve for accommodating said stem component, wherein said stem component is received in the axial channel so as to leave an annular gap between an outer surface of the stem component and the interior surface of said hollow sleeve.

7. The prosthetic system of claim 6, further comprising an adhesive located within said annular gap for securing said stem component in the axial channel.

8. The prosthetic system of claim 7, wherein said adhesive interdigitates into said porous structure.

9. The prosthetic system of claim 6, wherein said exterior surface of the hollow sleeve is sloped such that a first end of the hollow sleeve has a comparatively larger perimeter than a second end of the hollow sleeve.

10. The prosthetic system of claim 9, wherein said axial channel is sloped.

11. The prosthetic system of claim 6, wherein said hollow sleeve is cylindrical.

12. The prosthetic system of claim 11, wherein said hollow sleeve includes a first longitudinal section with a comparatively smaller diameter than a second longitudinal section of the hollow sleeve.

13. The prosthetic system of claim 6, wherein said interior surface of the hollow sleeve includes a corrugated surface.

14. The prosthetic system of claim 6, wherein said hollow sleeve is formed with a porous metal alloy.

15. A prosthetic system implantable in a cavity in an end of a bone, the prosthetic system comprising:
    a prosthetic implant including a stem component; and
    a hollow sleeve formed separately from said stem component for subsequent connection to said stem component, said hollow sleeve including an exterior surface securable to an inner surface of the cavity and an interior surface situated along an axial channel that extends through the length of the hollow sleeve for accommodating said stem component, said hollow sleeve formed with a bone ingrowth-receptive material with a porous structure for encouraging bone ingrowth into the hollow sleeve, with said bone ingrowth-receptive material providing both said exterior surface and said interior surface of the hollow sleeve, said hollow sleeve capable of being impacted into the cavity in the end of the bone for firmly wedging the hollow sleeve in the cavity prior to connecting said hollow sleeve to said stem component, wherein said stem component is received in the axial channel so as to leave an annular gap between an outer surface of the stem component and the interior surface of said hollow sleeve.

16. The prosthetic system of claim 15, further comprising an adhesive located within said annular gap for securing said stem component in the axial channel.

17. The prosthetic system of claim 15, wherein said exterior surface of the hollow sleeve is sloped such that a first end of the hollow sleeve has a comparatively larger perimeter than a second end of the hollow sleeve.

18. The prosthetic system of claim 15, wherein said hollow sleeve is cylindrical.

19. The prosthetic system of claim 18, wherein said hollow sleeve includes a first longitudinal section with a comparatively smaller diameter than a second longitudinal section of the hollow sleeve.

20. The prosthetic system of claim 15, wherein said interior surface of the hollow sleeve includes a textured or corrugated surface.

21. The prosthetic system of claim 15, wherein said hollow sleeve is formed with a porous metal alloy, a nonresorbable porous ceramic, a nonresorbable porous polymeric material, or a porous composite material.

22. The prosthetic system of claim 21, wherein said hollow sleeve is formed with a porous metal alloy.

23. The prosthetic system of claim 1, wherein said hollow sleeve has a sloped outer surface with a first end of the hollow sleeve having a comparatively larger perimeter than a second end of the hollow sleeve.

24. The prosthetic system of claim 23, wherein said axial channel is sloped.

25. The prosthetic system of claim 1, wherein said hollow sleeve is cylindrical.

26. The prosthetic system of claim 25, wherein said hollow sleeve includes a first longitudinal section with a comparatively smaller diameter than a second longitudinal section of the hollow sleeve.

27. The prosthetic system of claim 1, wherein said hollow sleeve is formed with a porous metal alloy, a nonresorbable porous ceramic, a nonresorbable porous polymeric material, or a porous composite material.

28. The prosthetic system of claim 27, wherein said hollow sleeve is formed with a porous metal alloy.

29. A prosthetic system for implantation in a cavity in an end of a bone, the prosthetic system comprising:
a prosthetic implant including a stem component; and
a hollow sleeve formed separately from said stem component for subsequent connection to said stem component, said hollow sleeve, while being a porous structure for encouraging bone ingrowth into the hollow sleeve, capable of being impacted into the cavity in the end of the bone for firmly wedging the hollow sleeve in the cavity prior to connecting said hollow sleeve to said stem component, said hollow sleeve including an axial channel that extends through the length of the hollow sleeve for accommodating said stem component, wherein said stem component is receivable in the axial channel so as to leave an annular gap between an outer surface of the stem component and an interior surface of the hollow sleeve that is situated along said axial channel.

30. A prosthetic system for implantation in a cavity in an end of a bone, the prosthetic system comprising:
a prosthetic implant including a stem component; and
a hollow sleeve formed separately from said stem component for subsequent connection to said stem component, wherein said hollow sleeve is a porous structure for encouraging bone ingrowth into the hollow sleeve and is capable of being impacted into the cavity in the end of the bone for firmly wedging the hollow sleeve in the cavity prior to connecting said hollow sleeve to said stem component, said hollow sleeve including an exterior surface and an interior surface with said interior surface situated along an axial channel that extends through the length of the hollow sleeve for accommodating said stem component, wherein said stem component is receivable in the axial channel so as to leave an annular gap between an outer surface of the stem component and the interior surface of said hollow sleeve.

* * * * *